(12) United States Patent
Burke et al.

(10) Patent No.: US 8,497,138 B2
(45) Date of Patent: Jul. 30, 2013

(54) METHOD FOR CELL SELECTION

(75) Inventors: Julian Burke, Hampshire (GB);
Alasdair Robertson, Hampshire (GB);
Xiao Zhang, Hampshire (GB)

(73) Assignee: Genetix Limited (GB)

( * ) Notice: Subject to any disclaimer, the term of this patent is extended or adjusted under 35 U.S.C. 154(b) by 248 days.

(21) Appl. No.: 12/895,273

(22) Filed: Sep. 30, 2010

(65) Prior Publication Data

US 2012/0082361 A1    Apr. 5, 2012

(51) Int. Cl.
*G01N 33/53* (2006.01)
*G01N 33/00* (2006.01)

(52) U.S. Cl.
USPC .......... 436/547; 435/7.1; 435/7.21; 435/7.94; 435/7.95; 435/326; 435/287.2; 436/513; 436/518; 436/535; 436/548; 436/63

(58) Field of Classification Search
USPC ............... 435/7.1, 7.21, 7.92, 7.95, 325, 326, 435/373, 397, 289.1, 7.94, 287.2; 436/513, 436/514, 518, 530, 546, 547, 548, 63, 535
See application file for complete search history.

(56) References Cited

U.S. PATENT DOCUMENTS

2007/0037220 A1 * 2/2007 Burke et al. ................... 435/7.2
2009/0239250 A1 * 9/2009 Klug et al. ...................... 435/29

OTHER PUBLICATIONS

Sharon et al. Detection of specific hybridoma clones by replica immunoadsorption of the secreted antibodies, Immunology 76 (3): 1420-1424 (Mar. 1999).*

* cited by examiner

*Primary Examiner* — Gail R Gabel
(74) *Attorney, Agent, or Firm* — James R. Abney; Bella Fishman

(57) ABSTRACT

In one aspect the present invention provides a method for selecting a cell or cell colony which produces a polypeptide of interest, comprising a) providing a medium comprising cells and a detection agent, wherein the detection agent is associated with a detectable signal and the detection agent is capable of binding to the polypeptide of interest; b) providing a solid phase having a capture agent disposed thereon, wherein the capture agent is capable of binding to the polypeptide of interest; c) contacting the medium with the solid phase; d) detecting the signal associated with the detection agent; and e) selecting a cell or cell colony associated with the signal, wherein presence of the signal is indicative of a cell or cell colony which produces the polypeptide of interest.

20 Claims, 16 Drawing Sheets

METHOD FOR CELL SELECTION

FIELD

The present invention relates to detecting cells which produce a polypeptide of interest, for instance during the selection of cultured cell colonies using an automated picking apparatus.

BACKGROUND

Many molecular biology techniques depend on cloning individual cells from a mixture of cells.

For example, in the production of monoclonal antibodies, an essential step is hybridoma selection, including the separation and culture of individual hybridoma clones (fused myelomas and primary mouse cells). After cell fusion, the traditional way of selecting for monoclonality is to plate out single cells into 96-well dishes. This is repeated until clonality is assured.

Similarly, understanding gene function and identification of pharmaceutical leads requires the establishment of cell lines containing transfected genes expressed at an appropriate level. Standard techniques require the co-transfection of a gene with a dominant selectable marker followed by selection for growth for example in an antibiotic such as G418 or hygromycin. The resulting colonies are then picked by hand and further analysed for gene expression (RT-PCR) and functional expression.

Ascertaining optimal conditions for cell growth and differentiation requires broad testing of growth factors and culture conditions. The evaluation of a particular treatment requires a statistical approach on a large number of individual cells. One way to achieve this is to use numerous culture dishes, several for each treatment.

This process of cloning out may be modified and automated through the use of robots. Thus, for example, the ClonePix robot (manufactured by Genetix) implements this process by picking individual colonies directly from standard semi-solid media, the media preventing migration of the dividing cells. Thus, an imaging head captures images of colonies growing in the medium under white light, and software routines allow the separation and detection of individual colonies. A picking head then picks individual colonies into a 96-well plate.

Using a robot implemented picking method, colonies can be picked into 96-well plates at a picking speed of up to 400 clones per hour and graphic software allows the user to select colonies on the basis of size, shape, brightness and proximity. Furthermore, the software allows stratification of clones into slow, medium and fast growing cells, and clones of the same class may be grouped in the same 96-well plate. This gives rise to considerable savings in subsequent tissue culture steps as all wells can be processed at the same time.

However, this robot implemented cloning method relies on visualisation solely of colony size. Thus, the image capture only provides information on the size of the colony, and all colonies within a certain size range are picked. It is known for example that different hybridoma clones are capable of producing varying amounts of antibody. No information is provided or processed as to the productivity of different cells (i.e., the quantity of product produced or secreted), and this robot implemented cloning method therefore cannot discriminate between a high-producing hybridoma cell or colony and a low-producing hybridoma cell or colony. With regard to transfected cells, the robot cannot distinguish between clones with different levels of expression and/or secretion of recombinant protein.

A method disclosed in EP1752771 addresses this issue by identifying cells producing a polypeptide of interest using a combination of a class marker and a specificity marker. Marker-polypeptide complexes can then be detected, for example by an automated imaging system, and cells producing a high level of the polypeptide picked directly by a robot. Application of the class marker limits the diffusion of the secreted polypeptide and causes the formation of a halo or aura of polypeptide surrounding the cell or cell colony. Formation of such a halo increases the effective concentration of the polypeptide in the vicinity of the cell or colony, to enable more efficient binding by the specificity marker to the polypeptide. This method may allow the application of a smaller amount or concentration of specificity marker compared to methods which do not make use of a class marker.

However, there is a still a need for improved methods for selecting cells or colonies which produce a polypeptide of interest.

SUMMARY

Accordingly, in one aspect the present invention provides a method for selecting a cell or cell colony which produces a polypeptide of interest, comprising a) providing a medium comprising cells and a detection agent, wherein the detection agent is associated with a detectable signal and the detection agent is capable of binding to the polypeptide of interest; b) providing a solid phase having a capture agent disposed thereon, wherein the capture agent is capable of binding to the polypeptide of interest; c) contacting the medium with the solid phase; d) detecting the signal associated with the detection agent; and e) selecting a cell or cell colony associated with the signal, wherein presence of the signal is indicative of a cell or cell colony which produces the polypeptide of interest.

In one embodiment the medium comprises a liquid medium, e.g. a liquid cell growth or culture medium. In another embodiment the medium comprises a solid or semi-solid medium, e.g. a semi-solid cell growth or culture medium.

In one embodiment, the step of selecting a cell or cell colony comprises picking a cell or cell colony which produces the polypeptide of interest. In further embodiments, the cell or cell colony may be selected by laser dissection, e.g. by dissecting a region of the medium using a laser dissection device.

In one embodiment, the step of detecting the signal comprises obtaining an image associated with the signal, and optionally further analysing the image to detect signal values above a predetermined level. In this embodiment, the method may comprise determining a signal level for each cell or cell colony based on signal values from a predefined area of the image comprising the cell or cell colony. Typically the signal level is indicative of the production level of the polypeptide of interest by the cell or cell colony.

In one embodiment, the cells or cell colonies are selected based on interior signal intensity values, e.g. interior mean intensity, interior total intensity or interior mean centre intensity values.

Preferably the image is obtained and analysed by an automated imaging system. In one embodiment, the signal is a fluorescent signal. In one embodiment, the cell or cell colony is picked by an automated cell picking device.

In one embodiment, the medium is removed or separated from the solid phase before detecting the signal derived from the detection agent bound to the solid phase.

Preferably the polypeptide of interest is a secreted polypeptide, e.g. the polypeptide is secreted by the cell or cell colony. In one embodiment the polypeptide of interest is an immunoglobulin, e.g. an IgG.

In specific embodiments the detection agent and/or the capture agent comprises an antibody or fragment thereof which binds selectively to the polypeptide of interest. The detection agent may further comprise a detectable reporter or label, e.g. a fluorescent label.

Preferably the solid phase comprises a culture dish, well or plate.

In a further aspect, the invention provides an automated cell picking, dissection and/or selection apparatus comprising (a) an automated imaging device; (b) a cell picking head or a laser dissection device; and (c) a sample comprising (i) a medium comprising cells and a detection agent, wherein the detection agent is associated with a detectable signal and the detection agent is capable of binding to a polypeptide of interest; and (ii) a solid phase having a capture agent disposed thereon, wherein the capture agent is capable of binding to the polypeptide of interest.

Preferably the sample is configured or arranged within the apparatus to be interrogated by the imaging device, laser dissection device and/or cell picking head. For instance the apparatus may be configured to (a) obtain an image of the sample and/or solid phase; (b) analyze the image to detect a signal associated with the detection agent; and (c) select a cell or cell colony associated with the signal, e.g. using the cell picking head or laser dissection device. In one embodiment, the imaging device comprises a fluorescent imaging device, a camera and a processor.

In embodiments of the present invention, a capture agent (e.g. an antibody specific for the polypeptide of interest) is disposed on a solid phase (e.g. a culture plate or dish). By coating the solid phase with the capture agent, the total amount of a secreted protein bound by the detection agent can be increased. Moreover, the methods of the present invention may increase the efficiency of capture of the secreted protein, by reducing diffusion of the secretion protein away from the colony which produces it. By increasing the local concentration of the secreted protein in the vicinity of the colony, the local signal intensity produced by the detection agent in the region of the colony can be increased, thereby facilitating the identification of colonies which produce the polypeptide of interest.

DETAILED DESCRIPTION

Figure 1:
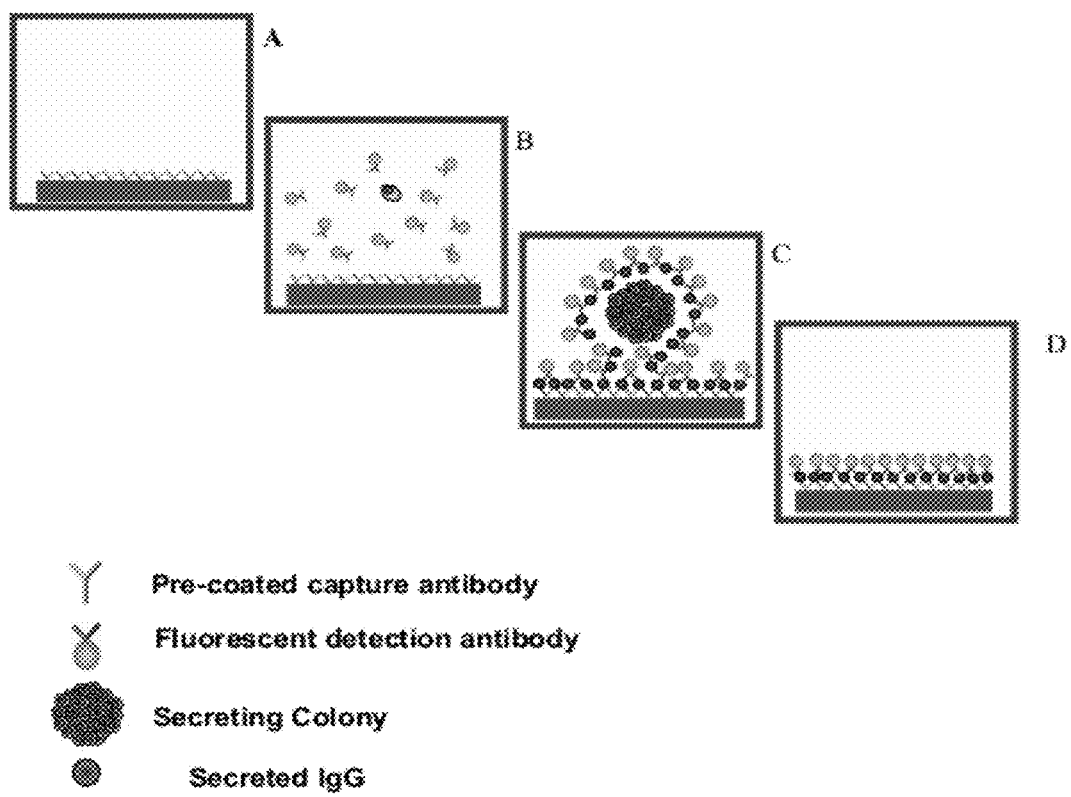
FIGS. 1A-1D show a schematic representation of one embodiment of the present method, with FIG. 1A depicting a plate pre-coated with unlabelled capture antibody, FIG. 1B depicting cells plated in a semi-solid medium with a labeled detection antibody, FIG. 1C depicting secreted IgG captured locally around a colony by the capture antibody and the detection antibody, and FIG. 1D depicting a configuration produced by picking the colony and washing the medium off the plate before the plate is imaged.

The present invention provides a method of selecting a cell or colony which produces a polypeptide of interest. A capture agent is used to bind the polypeptide of interest to a solid phase. A detection agent is used to identify cells or colonies which produce the polypeptide of interest. The detection agent may be labelled with a reporter which is capable of emitting a signal in order to ease detection. Colonies or cells of interest may then be selected and picked for further study.

Cell or Cell Colony

The cell or colony of cells may comprise any cultured cell or cell line, as known in the art. Included are prokaryotic cells and eukaryotic cells, including bacteria, yeast, insect and mammalian cells. A list of known cell lines is set out in the Cell Line Data Base (Istituto Nazionale per la Ricerca sul Cancro, Genova, Italy) and the ECACC European Collection of Cell Cultures. Specific examples of cells include *E. coli* cells, CHO cells, HeLa cells, African green monkey cells, SD cells, etc. Such cells may be transfected with suitable expression vectors to enable expression of polypeptides, as described in further detail below. Other cells particularly suitable for use in the methods described here are fused cell lines, including hybridoma cell lines.

In general, when referring to "a cell" herein, unless otherwise stated it is intended to include more than one cell, a plurality of cells, or any collection of cells, e.g. a cell colony. Thus "a method of selecting a cell" includes a method of selecting two or more cells or a colony of cells (e.g. which produce a polypeptide of interest). The method can therefore be applied to picking cell colonies as well as to identifying individual cells which express a polypeptide of interest.

Polypeptide of Interest

The polypeptide of interest may be, for example, an intracellular polypeptide, a membrane polypeptide or a secreted polypeptide. In one embodiment, the polypeptide of interest is a secreted polypeptide, e.g. a secreted antibody such as IgG. The secreted polypeptide may form a halo or aura around the cell or colony which produces it. However, in embodiments of the present invention, the presence of the capture agent bound to the solid phase may reduce the size or extent of the halo or aura.

Preferably the polypeptide of interest is a biotherapeutic molecule, for instance a therapeutic antibody, growth factor, cytokine or other recombinant polypeptide expressed by the cell. In one embodiment, the polypeptide of interest is a recombinant polypeptide expressed by a host cell, i.e. the cell has been engineered to express the polypeptide of interest.

Exemplary polypeptides of interest include antibodies, peptibodies, immunoglobulin-like proteins, non-antibody proteins and non-immunoglobulin-like proteins, particularly biotherapeutic molecules in these classes. Such polypeptides include those with modified glycosylation, polypeptides without glycosylation (unglycosylated). As used herein, "analogs" refers to an amino acid sequence that has insertions, deletions or substitutions relative to the parent sequence, while still substantially maintaining the biological activity of the parent sequence, as determined using biological assays known to one of skill in the art. Polypeptides of interest also include derivatives of naturally occurring or analog polypeptides which have been chemically modified, for example, to attach water soluble polymers (e.g., pegylated), radionuclides, or other diagnostic or targeting or therapeutic moieties.

Exemplary polypeptides of interest include human erythropoietin, darbepoetin, granulocyte-colony stimulating factor (GCSF), stem cell factor, leptin, hormones, cytokines, hematopoietic factors, growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, or kallikrein, receptors or soluble receptors, enzymes, variants, derivatives, or analogs of any of these proteins.

In one embodiment, the polypeptide of interest comprises an antibody or immunoglobulin. Thus one aspect of the invention provides a method of detecting a polypeptide of interest comprising an antibody or immunoglobulin produced by a cell or cell colony. The cell or cell colony may therefore comprise an antibody producing cell, preferably an antibody secreting cell, such as a B-cell, transfected myeloma or a hybridoma.

As used herein, the term "antibody" includes fully assembled antibodies, monoclonal antibodies (including human, humanized or chimeric antibodies), multispecific antibodies (e.g., bispecific antibodies), Maxibody, and antibody fragments that can bind antigen (e.g., Fab', F'(ab)2, Fv, single chain antibodies, diabodies), comprising complementarity determining regions (CDRs) of the foregoing as long as they exhibit the desired biological activity.

Exemplary antibodies are Herceptin® (Trastuzumab), a recombinant DNA-derived humanized monoclonal antibody that selectively binds to the extracellular domain of the human epidermal growth factor receptor 2 (Her2) proto-oncogene; Rituxan® (Rituximab), a genetically engineered chimeric murine/human monoclonal antibody directed against the CD20 antigen found on the surface of normal and malignant B lymphocytes; Avastin® (bevacizumab), Bexxar® (Tositumomab), Campath® (Alemtuzumab), Erbitux® (Cetuximab), Humira® (Adalimumab), Raptiva® (efalizumab), Remicade® (Infliximab), ReoPro® (Abciximab), Simulect® (Basiliximab), Synagis® (Palivizumab), Xolair® (Omalizumab), Zenapax® (Daclizumab), Zevalin® (Ibritumomab Tiuxetan), or Mylotarg® (gemtuzumab ozogamicin), receptors or soluble receptors, enzymes, variants, derivatives, or analogs of any of these antibodies.

In one embodiment, the polypeptide of interest comprises a receptor polypeptide. A receptor, as the term is used in this document, means any polypeptide which is capable of binding another molecule, preferably a small molecule such as a ligand. Preferably, a receptor is a protein molecule that receives and responds to a specific neurotransmitter, hormone, ligand or other substance. Preferably, the receptor is capable of binding an affinity ligand of the receptor.

Where the polypeptide comprises a receptor, the cell or cell colony may be a cultured cell which has been engineered to express the receptor, preferably as a recombinant protein. The cell which is transfected may be any suitable cell as known in the art, for example, suspension adapted adherent cells such as CHO—S are suitable.

The cell may be transfected with an expression vector encoding a receptor polypeptide. The receptor preferably comprises a trans-membrane receptor, and may be a peripheral membrane receptor, a transmembrane protein receptor or an intracellular receptor, such as a nuclear receptor.

The receptor may comprise a G protein-coupled receptor (GPCR), also known as a seven transmembrane receptor or 7TM receptor. For example, the receptor may comprise any of the following (ligands in brackets following): a "muscarinic" acetylcholine receptor (acetylcholine and muscarine), an adenosine receptor (adenosine), an adrenoceptor or adrenergic receptor (ligand: adrenaline, and other structurally related hormones and drugs), a GABA receptor, type-b (γ-aminobutyric acid or GABA), an angiotensin receptor (angiotensin), a cannabinoid receptor (cannabinoids), a cholecystokinin receptor (cholecystokinin), a dopamine receptor (dopamine), a glucagon receptor (glucagon), a histamine receptor (histamine), a olfactory receptor, a opioid receptor (opioids), a rhodopsin (a photoreceptor), a secretin receptor (secretin), a serotonin receptors (Serotonin, also known as 5-Hydroxytryptamine or 5-HT) or a somatostatin receptor (Somatostatin).

The receptor may comprise a tyrosine kinase receptor, such as an erythropoietin receptor (Erythropoietin), an insulin receptor (Insulin), a growth factor receptor or a cytokine receptor. The receptor may comprise a guanylyl cyclase receptor such as GC-A & GC-B, comprising receptors for Atrial-natriuretic peptide (ANP) and other natriuretic peptides or GC-C, a guanylin receptor.

The receptor may comprise an ionotropic receptor, for example a nicotinic acetylcholine receptor (Acetylcholine, Nicotine), a glycine receptor (GlyR) (Glycine, Strychnine), a GABA receptor: GABA-A, GABA-C (GABA), a glutamate receptor, an NMDA receptor, an AMPA receptor, a kainate receptor (Glutamate) or a 5-HT3 receptor (Serotonin).

Medium

In embodiments of the present invention, the cells are provided in a medium which may further comprise the detection agent. Various types of media suitable for the culture of cells and cell colonies may be used, including known liquid, semi-solid and solid cell culture media.

In one embodiment, the cells are grown on the surface of or within solid or semi-solid media. Growth of cells, particularly antibody secreting hybridomas, on such media enhances secretion, as described in Goding, J. W. 1980, Antibody production by hybridomas, J. Immunol. Methods. 39(4): 285-308; Sharon, J., Morrison, S. L. and Kabat, E. A. 1979, Detection of specific hybridoma clones by replica immunoadsorption of their secreted antibodies, Proc. Natl. Acad. Sci. (USA). 76(3): 1420-4; and Davis, J. M., Pennington, J. E., Kubler, A.-M. and Conscience, J. F. 1982, A simple, single-step technique for selecting and cloning hybridomas for the production of monoclonal antibodies, J. Immunol. Methods. 50: 161-171.

Methylcellulose media may, for example, be obtained from Sigma-Aldrich Company Ltd (Dorset, UK) under catalogue number M0387 (Methyl cellulose viscosity 1,500 cP (2% aqueous solution, 20° C.) (lit.) CAS Number 9004-67-5) or catalogue number M0512 (Methyl cellulose viscosity 4,000 cP (2% aqueous solution, 20° C.) (lit.) CAS Number 9004-67-5).

In some embodiments, the polypeptide of interest is secreted from a cell or colony of cells grown on the surface of or within methylcellulose media. The use of methylcellulose media is well known in the art, and protocols have been established to enable hybridoma cloning on such media. See for example, the ClonaCell™-HY Hybridoma Cloning Kit Procedure Manual (StemCell Technologies, Vancouver, Canada), herein incorporated by reference.

In some embodiments, the polypeptide of interest may be secreted into the medium such that it surrounds the cell or colony to form a halo or aura. Thus, the halo or aura in general terms comprises a concentration of polypeptide in the immediate environs of the cell or colony. Haloes or auras are particularly pronounced so where the cell or colony is growing on the surface of or within a solid or semi-solid medium. The halo or aura arises through the fact that diffusion of the secreted polypeptide away from the cell or colony producing it is restricted. Typically the presence of the capture agent on the solid phase reduces the size, area or extent of the halo or aura.

In alternative embodiments, the medium is a liquid medium. Various liquid media for the growth and/or expansion of cells are known in the art, e.g. XP Media CHO (a liquid medium for CHO—S cells available from Genetix Ltd, New Milton, UK), Dulbecco's Modified Eagle Medium (DMEM), Roswell Park Memorial Institute (RPMI) 1640 medium; bacterial culture media such as LB, NZCYM, NZYM, NZM, Terrific Broth, SOB, SOC, 2×YT, or M9 Minimal Medium; and yeast culture media such as YPD, YEPD, Minimal Medium, or Complete Minimal Dropout Medium.

The medium may optionally comprise growth factors or other supplements optimized to support the selection and growth of the relevant cells. For instance, the medium may further comprise a mammalian serum, for example foetal calf serum, or trace elements and growth sustaining supplements, for example feeder cells such as normal mouse peritoneal exudate cells, spleen cells, bone marrow macrophages, 2-aminoethanol, insulin, transferrin, low density lipoprotein, oleic acid, or the like. The culture medium may be serum-free or animal-produce free, such as a chemically defined medium, in order to minimise animal derived contamination.

In one embodiment, the medium is a liquid or semi-solid medium as described in EP1818392.

Detection Agent

The detection agent is capable of binding to the polypeptide of interest and is associated with a detectable signal. For instance, the detection agent may be any compound which binds specifically or selectively to the polypeptide of interest. The detection agent may produce a detectable signal directly or indirectly, e.g. the detection agent may comprise a detectable reporter or label, or a further compound comprising the detectable reporter or label may bind specifically or selectively to the detection agent.

In some embodiments, the detection agent may comprise a compound having affinity or specificity for a class of polypeptides to which the polypeptide of interest belongs. For example, where the class of polypeptide comprises immunoglobulins, the detection agent may comprise Protein A or Protein G. Protein A is a surface protein of *Staphylococcus aureus* which binds to IgG molecules via their Fc regions.

Alternatively, the detection agent may comprise a specific binding partner of the polypeptide of interest. In such embodiments, the polypeptide of interest has a specific binding affinity for the detection agent; in other words, detection agent is capable of being specifically bound by a polypeptide of interest. For example, in one embodiment substantially only the polypeptide of interest binds that detection agent. Preferably, no other polypeptide, for example an unrelated polypeptide to the polypeptide of interest, binds that detection agent.

In one embodiment, the polypeptide of interest in an immunoglobulin (e.g. an antibody or a fragment thereof) and the detection agent comprises an antigen or epitope recognised by the immunoglobulin. For example, the detection agent may comprise an antigen to which the immunoglobulin binds specifically or selectively.

In other embodiments the detection agent comprises an antibody or immunoglobulin which binds to the polypeptide of interest. For example, the detection agent may comprise an antibody which is capable of specifically binding to the polypeptide of interest, or to a conserved domain or epitope which is shared by members of the class of polypeptides to which the polypeptide of interest belongs.

For instance, in one embodiment the detection agent comprises an immunoglobulin which binds to an antibody class or an antibody isotype of interest. In preferred embodiments, the antibody class comprises an Ig class such as an IgG class, an IgA class, an IgM class, an IgD class or an IgE class. In other embodiments, the polypeptide class may comprise an immunoglobulin subclass. For example, the polypeptide class may comprise an IgG subclass including an IgG1 subclass, an IgG2 subclass, an IgG3 subclass or an IgG4 subclass. The polypeptide class may comprise an IgA subclass such as an IgA1 subclass or an IgA2 subclass. Such antibodies may be directed against any suitable common motif or sequence present in the Ig class of interest. Examples of such common motifs and sequences include the constant regions of a heavy chain, including gamma (γ), alpha (α), mu (μ), delta (δ) and epsilon (ε) regions. Other regions suitable for use include constant regions of a light chain, including lambda (λ) and kappa (κ) regions.

In preferred embodiments, the detection agent comprises a binding agent capable of binding to an IgG class such as an anti-IgG antibody, preferably a specific anti-IgG antibody. Thus, for example, a detection agent specific for the IgG isotype may be generated in the form of an antibody (from another species) raised against a γ chain. Antibodies specific for antibody Ig classes are well known in the art and are available commercially.

The detection agent may comprise a polyclonal antibody or a monoclonal antibody, which may be engineered. In some embodiments, the detection agent comprises a polyclonal antibody, such as a goat or rabbit anti-polypeptide antibody raised for example against a mouse or human IgG. The antibody may be whole, or it may comprise a fragment thereof, preferably a binding fragment such as a F(ab')$_2$ fragment. Where the term antibody is used in this document, it should be taken to include such fragments.

In some embodiments, the detection agent comprises a small molecule, e.g. a molecule which has a molecular weight below 50 kDa, below 10 kDa, below 1 kDa, or below 100 Da. In one embodiment the detection agent comprises an organic molecule. The detection agent may comprise any of the known biomolecules which exist in organisms, such as hormones, peptides, amino acids, nucleic acids, etc., and may be synthetic or natural.

In some embodiments, multiple detection agents may be used. Multiple detection agents may be employed for example in the case where it is desired to detect two or more polypeptides of interest, e.g. where the medium comprises cells which are transfected with two or more different expression vectors expressing different transfected polypeptides. In one embodiment, the use of multiple detection agents enables the detection of variants (i.e., mutants, etc) of a polypeptide of interest. The multiple detection agents may have different specificity, one for each of the variants it is desired to detect.

Signal

The detection agent is capable of being detected, preferably by emitting a signal. For this purpose, the detection agent may be labelled with a reporter molecule. A "signal", as used here, is any detectable event. The signal may be the generation of an enzymatic activity, such as protease activity, transcriptional activity or luminescence inducing activity. Preferably, however, the signal is emission or absorption of electromagnetic radiation, for example, light.

In highly preferred embodiments, the signal is a fluorescent signal. Included are fluorescence, phosphorescence or other signals which involve the modulation of the intensity or frequency of emission or absorption of radiation, for example, a FRET signal (described in further detail below).

Preferably, the fluorescent signal is emitted from a fluorophore such as a fluorescent protein or fluorescent chemical. Thus, detection agent may comprise a reporter molecule comprising a fluorophore such as a fluorescent protein or fluorescent chemical.

Examples of fluorescent chemicals include allophycocyanine, phycocyanine, phycoerythrin, rhodamine, tetramethyl rhodamine, 7-nitro-benzofurazan rhodamine isothiocyanate, oxazine, coumarin, fluorescein derivatives, for example, FAM (6-carboxy-fluorescein), TET (6-carboxy-4,7,2',7'-tetrachloro-fluorescein), (FITC) fluorescein isothiocyanate and carboxyfluorescein diacetate, as well as Texas Red, acridine yellow/orange, ethidium bromide, propidium iodide and bis-benzamide (commercially available from Hoechst under the trade name H33258).

Preferred fluorescent chemicals are fluorescein isothiocyanate, rhodamine and phycoerythrin, and preferred fluorescent proteins are Green Fluorescent Protein, Blue Fluorescent Protein, Cyan Fluorescent Protein, Yellow Fluorescent Protein and Red Fluorescent Protein. The fluorescent signal may be modulated by fluorescent resonance energy transfer (FRET). Methods of conjugating fluorescent labels to various entities, including peptides, polypeptides and antibodies, are well known in the art.

The fluorescent signal may be emitted from a fluorescent polypeptide. Thus, the detection agent may comprise a reporter molecule comprising a fluorescent polypeptide. Examples of fluorescent polypeptides and proteins include Green Fluorescent Protein (GFP) from *Aequorea victoria* and Red Fluorescent Protein (RFP) from *Discosoma* spp. Derivatives and variants of these proteins, such as Cyan Fluorescent Protein, Blue Fluorescent Protein, Enhanced Green Fluorescent Protein (EGFP; GFPmut1; Yang, T. T., et al. (1996) Nucleic Acids Res. 24(22):4592-4593; Cormack, B. P., et al. (1996) Gene 173:33-38.), Enhanced Blue Fluorescent Protein (EBFP), Enhanced Yellow Fluorescent Protein (EYFP; Ormö, et al. (1996) Science 273:1392-1395), Destablised Enhanced Green Fluorescent Protein (d2EGFP; Living Colors Destabilized EGFP Vectors (April 1998) CLONTECHniques XIII(2):16-17), Enhanced Cyan Fluorescent Protein (ECFP), and GFPuv (Haas, J., et al. (1996) Curr. Biol. 6:315-324) may also be used. These fluorescent proteins are available from CLONTECH Laboratories, Inc. (Palo Alto, Calif., USA).

The signal may be a luminescence inducing activity. It will be appreciated that as light is generated during luminescence, the signal may at the same time be a luminescence inducing activity and emission of electromagnetic radiation.

The signal may also be the generation of an enzymatic activity, for example, transcriptional activity. The detection agent may therefore comprise a polypeptide with an assayable enzyme activity. Where the enzyme activity comprises transcriptional activity, this may be detected by assaying the expression of a reporter gene such as CD4, by fluorescent antibodies and FACs for example.

The reporter may be attached, coupled, fused, mixed, combined, or otherwise joined to the detection agent. The attachment, etc between the reporter and the detection agent may be permanent or transient, and may involve covalent or non-covalent interactions (including hydrogen bonding, ionic interactions, hydrophobic forces, Van der Waals interactions, etc).

In preferred embodiments, the reporter is permanently, preferably covalently attached to the detection agent. In such preferred embodiments, the reporter is chemically coupled or cross-linked to the detection agent. Any of the various methods of chemical coupling which are known in the art may be employed for this purpose.

In certain embodiments, it may be desirable to include spacing means between the reporter and the detection agent. Such spacing means may suitably comprise linkers or spacers as known in the art. The purpose of the spacing means is to space the reporter and the marker, to avoid for example steric hindrance and to promote detection of the reporter and hence the detection agent. Accordingly, depending on the application, the use of shorter or longer spacers may be preferred.

The spacing means may comprise linkers or spacers which are polymers of differing lengths (the length of which may be controlled by controlling the degree of polymerisation). Numerous spacers and linkers are known in the art, and the skilled person will know how to choose and use these, depending on the application. The skilled person will also know what spacer length to use.

The spacers may be made for example of polyethylenglycol, PEG derivatives or polyalkanes or homo poly amino acids. Dextrans and dendrimers, as known in the art, may also be used. In particular, the linkers or spacers may comprise nucleotide polymers (nucleic acids, polynucleotides, etc) or amino acid polymers (proteins, peptides, polypeptides, etc).

Solid Phase

Embodiments of the present invention may employ a solid phase on which the capture agent is disposed. By "solid phase" it is typically meant any solid surface, such as a surface (e.g. walls and/or base) of a vessel within which the medium may be disposed or contained. In one embodiment, the solid phase comprises a planar substrate, e.g. a culture dish or plate. For instance, the solid phase may be a Petri dish, a well plate or other similar container, e.g. a single well plate, a 4 well plate, a 6 well plate, a microtitre dish or the like. Thus as used herein, the solid phase is distinct from the medium comprising the cells, even where the medium is solid or semi-solid.

The composition of the solid phase is not particularly limited, e.g. the solid phase can be made of any insoluble or solid material. Typically the solid phase is composed of glass or a plastic, e.g. from a polymer such as polystyrene, polycarbonate, polyethylene, polypropylene, polyamide, polyacrylamide, or polyvinylidenedifluoride.

Capture Agent

The capture agent is capable of binding to the polypeptide of interest. For instance, the capture agent may be any compound which binds specifically or selectively to the polypeptide of interest, e.g. as described above in relation to the detection agent.

Thus in particular embodiments, the capture agent may comprise a compound having affinity or specificity for a class of polypeptides to which the polypeptide of interest belongs, e.g. Protein A or Protein G. In another embodiment, the capture agent may comprise a specific binding partner of the polypeptide of interest.

In one embodiment, the polypeptide of interest in an immunoglobulin (e.g. an antibody or a fragment thereof) and the capture agent comprises an antigen or epitope recognised by the immunoglobulin. For example, the capture agent may comprise an antigen to which the immunoglobulin binds specifically or selectively.

In other embodiments the capture agent comprises an antibody or immunoglobulin which binds to the polypeptide of interest. For example, the capture agent may comprise an antibody which is capable of specifically binding to the polypeptide of interest, or to a conserved domain or epitope which is shared by members of the class of polypeptides to which the polypeptide of interest belongs. The capture agent may comprise a polyclonal antibody or a monoclonal antibody, or a fragment thereof.

In other embodiments, the capture agent comprises a small molecule, e.g. a molecule which has a molecular weight below 50 kDa, below 10 kDa, below 1 kDa, or below 100 Da. The capture agent may comprise an organic molecule. The capture agent may comprise any of the known biomolecules which exist in organisms, such as hormones, peptides, amino acids, nucleic acids, etc., and may be synthetic or natural. In some embodiments, multiple capture agents may be used.

The capture agent is disposed on the solid phase. By this it is typically meant that the capture agent is bound to, or located on, a surface of the solid phase, e.g. on the base and/or walls of a culture plate or dish. The capture agent may be attached, coupled, fused, mixed, combined, or otherwise joined to solid phase. The interaction between the capture agent and the solid phase may be permanent or transient, and may involve covalent or non-covalent interactions (including hydrogen bonding, ionic interactions, hydrophobic forces, Van der Waals interactions, etc). Typically the capture agent is applied to the solid phase (e.g. well plate or culture dish) by coating, i.e. the solid phase is coated with the capture agent. Methods for coating compounds such as antibodies onto surfaces (e.g. glass or plastic surfaces used in cell culture) are well known in the art. Suitable reagents and buffers for coating are available commercially, e.g. from ImmunoChemistry Technologies, Bloomington, Minn.

Antibodies

In certain embodiments, the polypeptide of interest may be an antibody. Moreover, the capture agent or the detection agent may be an antibody which binds to the polypeptide of interest.

Antibodies comprise immunoglobulin molecules. Immunoglobulin molecules are in the broadest sense members of the immunoglobulin superfamily, a family of polypeptides comprising the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The methods described here may therefore make use of any immunoglobulin superfamily molecule which is capable of binding to a target molecule. Peptides or fragments derived from immunoglobulins may also be used.

Antibodies, as used herein, refers to complete antibodies or antibody fragments capable of binding to a selected target, and including Fv, scFv, F(ab') and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and scFv, possess advantageous properties for diagnostic and therapeutic applications on account of their small size and consequent superior tissue distribution. Preferably, the antibody is a single chain antibody or scFv.

Antibodies to be used as capture or detection agents may be obtained from animal serum, or, in the case of monoclonal antibodies or fragments thereof, produced in cell culture. Recombinant DNA technology may be used to produce the antibodies according to established procedure, in bacterial, yeast, insect or preferably mammalian cell culture. The selected cell culture system preferably secretes the antibody product.

Growing of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, for example foetal calf serum, or trace elements and growth sustaining supplements, for example feeder cells such as normal mouse peritoneal exudate cells, spleen cells, bone marrow macrophages, 2-aminoethanol, insulin, transferrin, low density lipoprotein, oleic acid, or the like. The culture medium may be serum-free or animal-produce free, such as a chemically defined medium, in order to minimise animal derived contamination. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

Use of insect cells as hosts for the expression of proteins has advantages in that the cloning and expression process is relatively easy and quick. In addition, there is a high probability of obtaining a correctly folded and biologically active protein when compared to bacterial or yeast expression. Insect cells may be cultured in serum free medium, which is cheaper and safer compared to serum containing medium. Recombinant baculovirus may be used as an expression vector, and the construct used to transfect a host cell line, which may be any of a number of lepidopteran cell lines, in particular *Spodoptera frugiperda Sf9*, as known in the art. Reviews of expression of recombinant proteins in insect host cells are provided by Altmann et al. (1999), *Glycoconj J* 1999, 16, 109-23 and Kost and Condreay (1999), *Curr Opin Biotechnol*, 10, 428-33.

In vitro production provides relatively pure antibody preparations and allows scale-up to give large amounts of the desired antibodies. Techniques for bacterial cell, yeast, insect and mammalian cell cultivation are known in the art and include homogeneous suspension culture, for example in an airlift reactor or in a continuous stirrer reactor, or immobilised or entrapped cell culture, for example in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, for example a sandwich assay or a dot-assay, or a radioimmunoassay.

For isolation of the antibodies, the immunoglobulins in the culture supernatants or in the ascitic fluid may be concentrated, for example by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or immunoaffinity chromatography, for example affinity chromatography with the a protein containing a target or with Protein-A.

Antibodies generated according to the foregoing procedures may be cloned by isolation of nucleic acid from cells, according to standard procedures. Usefully, nucleic acids variable domains of the antibodies may be isolated and used to construct antibody fragments, such as scFv.

The methods described here preferably employ recombinant nucleic acids comprising an insert coding for a heavy chain variable domain and/or for a light chain variable domain of antibodies. By definition such nucleic acids comprise coding single stranded nucleic acids, double stranded nucleic acids consisting of the coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised nucleic acids having the authentic sequence coding for a naturally-occurring heavy chain variable domain and/or for the light chain variable domain, or a mutant thereof. A mutant of the authentic sequence is a nucleic acid encoding a heavy chain variable domain and/or a light chain variable domain of the above-mentioned antibodies in which one or more amino acids are deleted or exchanged with one or more other amino acids. Preferably the modification(s) are outside the complementary determining regions (CDRs) of the heavy chain variable domain and/or of the light chain variable domain of the antibody. Such a mutant nucleic acid is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or a light chain variable domain.

The term mutant is intended to include a DNA mutant obtained by in vitro or in vivo mutagenesis of DNA according to methods known in the art.

Recombinant DNA technology may be used to improve antibodies. Thus, chimeric antibodies may be constructed in order to decrease the immunogenicity thereof in diagnostic or therapeutic applications. Moreover, immunogenicity may be minimised by humanising the antibodies by CDR grafting [European Patent 0 239 400 (Winter)] and, optionally, framework modification [European Patent 0239400; Riechmann et al., (1988) Nature 322:323-327; and as reviewed in international patent application WO 90/07861 (Protein Design Labs)].

Recombinant nucleic acids may be employed comprising an insert coding for a heavy chain variable domain of an antibody fused to a human constant domain γ, for example γ1, γ2, γ3 or γ4, preferably γ1 or γ4. Likewise recombinant DNAs comprising an insert coding for a light chain variable domain of an antibody fused to a human constant domain κ or λ, preferably κ may also be used.

More preferably, CDR-grafted antibodies, which are preferably CDR-grafted light chain and heavy chain variable domains only, may be used. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as scFvs.

Antibodies may moreover be generated by mutagenesis of antibody genes to produce artificial repertoires of antibodies. This technique allows the preparation of antibody libraries, as discussed further below; antibody libraries are also available commercially. Hence, artificial repertoires of immunoglobulins, preferably artificial ScFv repertoires, are used as an immunoglobulin source.

Isolated or cloned antibodies may be linked to other molecules, for example nucleic acid or protein association means by chemical coupling, using protocols known in the art (for example, Harlow and Lane, Antibodies: a Laboratory Manual, (1988) Cold Spring Harbor, and Maniatis, T., Fritsch, E. F. and Sambrook, J. (1991), Molecular Cloning: A Laboratory Manual. Cold Spring Harbor, N.Y., Cold Spring Harbor Laboratory Press).

Contacting the Medium with the Solid Phase

The method comprises a step of contacting the medium (comprising the cells) with the solid phase (on which the capture agent is disposed). For instance, this step may comprise plating the cells onto a culture dish or well plate which has been coated with the capture agent. Typically the detection agent is included in the medium which is plated onto the solid phase, i.e. the plating medium comprises cells and the detection agent. Alternatively, the detection agent may be added to the medium after the cells have been contacted with the solid phase, e.g. after plating the cells onto a surface coated with the capture agent. Thus the order in which steps (a) to (c) of the method are performed is not particularly limited, provided that at some point in the method, a solid phase with a capture agent disposed thereon is contacted with a medium comprising cells and a detection agent.

In one embodiment, the method comprises an incubation step after contacting the solid phase with the medium (and before the detection step). Typically the incubation step comprises allowing the cells or cell colonies in the medium to grow and/or secrete the polypeptide of interest, e.g. under suitable conditions and for a period of time suitable to allow production of detectable quantities of the polypeptide of interest. For example, the cells may be incubated in the medium on the solid phase for about 12 hours to 50 days, e.g. about 1 to 25 days, e.g. 5 to 15 days.

Detecting a Signal and Selecting Cells

The signal associated with the detection agent may be detecting using any suitable method or apparatus, e.g. depending on the nature of the reporter and/or label. For example, where the label is a fluorescent label, the signal may be detecting using a fluorescent microscope or any other fluorescent imaging apparatus.

In one embodiment, the signal is detected using an automated imaging apparatus. Such an apparatus may comprise a fluorescent imaging device such as a fluorescent microscope, and optionally an image acquisition device such as a camera, e.g. a CCD device. The apparatus may further comprise a processor, for example for processing the acquired image to determine the signal level.

Typically the selection step comprises picking one or more cells or cell colonies which produce the polypeptide of interest, e.g. using an automated cell picking device. In one embodiment, the automated cell picking device comprises an automated imaging apparatus as described above, and a cell picking head. The cell picking device may be configured to pick a cell or cell colony identified by the imaging apparatus, e.g. a cell or colony which has been identified as producing the polypeptide of interest at an elevated level.

The automated image and/or cell picking apparatus may be controlled by software, e.g. a computer program residing on a computer-readable medium. The computer program may comprise instructions for causing the apparatus (e.g. an imaging and/or cell picking apparatus) to obtain an image of the cells or cell colonies, analyze the image to detect a signal associated with the detection agent, and/or analyze signal values to detect a cell or cell colony which produces the polypeptide of interest. The computer program may further comprise instructions for causing the apparatus to pick one or more cells or cell colonies based on the indicated production level.

In preferred embodiments, any of the steps of the method, such as contacting the medium with the solid phase, detecting the signal, selecting and/or picking of cells or colonies of interest may be conducted using automated robotic apparatus. In preferred embodiments, the robotic apparatus comprises a ClonePix FL apparatus (Genetix, New Milton, United Kingdom).

Features of a robotic apparatus which are advantageous for the performance of the methods described here, and which are present in the ClonePixFL apparatus, include any one or more of the following: cool white light illumination; up to 5 fluorescence combinations; high-resolution cooled CCD camera; ability to image at standard pixel resolution of 7 µm permitting fluorescent detection of colonies with as few as 10 cells; image zooming to 1 µm resolution for detailed colony inspection; ability to pick colonies at up to 400 clones per hour; easy-to-use custom software (ExCellerate) for intelligent picking, Halo Recognition, barcoding and clone-by-clone data tracking; stackers hold up to 10 source and collection plates, and optional Class II-type containment.

The ClonePixFL apparatus is described in detail below.

Figure 13:
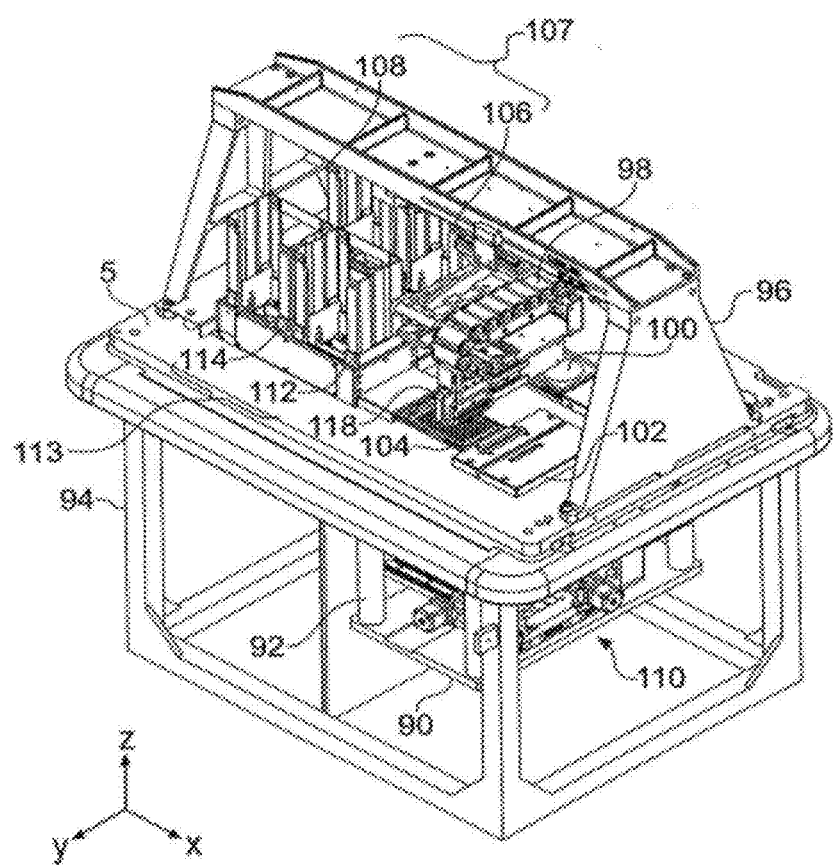
FIG. 13 is a perspective view of a robotic apparatus for carrying out methods according to the invention.

FIG. 13 is a perspective view of the ClonePixFL robotic platform for carrying out methods of the invention in an automated way. The apparatus may be considered to be a robot for picking, gel coring or other biological manipulation task with integrated fluorescence excitation and collection (i.e. detection) optics. The apparatus can be subdivided notionally into two half spaces existing above and below a main bed 5 which is supported by a frame 94.

Above the main bed 5, the apparatus appears as similar to a conventional picking robot. A cell picking head 118 is provided that comprises a plurality of hollow pins for aspirating animal cells. The cell picking head 118 is movable over the main bed 5 by a head position system made up of x-, y- and z-linear positioners 98 connected in series and suspended from a gantry 96. A wash/dry station 102 is also provided on the main bed 5 for cleansing the pins. The whole upper half space of the apparatus will typically be enclosed in a housing (not shown) including a hinged door extending over one side and part of the top of the apparatus.

Below the main bed 5, an optics sub-assembly 110 is provided to accommodate fluorescence excitation and detection optics system which is mounted on a tray 90 suspended from the main bed 5 by pillars 92. The under-slung optics system is arranged to view containers such as Petri dishes and well plates placed on the imaging station 100.

In use in the performance of the detection method described in this document, a Petri dish or other container (not shown) containing cells or colonies producing polypeptides (some of interest) is placed on the imaging station 100. Such containers are referred to for convenience generically as "well plates" in the following description, although it will be evident that they need not comprise wells. Thus, where the term "plate" or "well plate" is employed, it should be understood as encompassing any container suitable for growing cells, such as Petri dishes, microtitre dishes, 6 well plates, etc.

The main bed 5 is provided with two main working stations, namely an imaging station 100 and a replating station 104, each of which is positioned at the end of a respective well plate feed lane. Each well plate feed lane has a well plate feeder/stacker. The well plate feeder/stacker 107 for the imaging station 100 has a well plate feed storage cassette 106 and well plate (re-)stack storage cassette 108. A stack of well plates are held in the feed storage cassette 106, fed in turn down the lane via a delidder (not shown) to the imaging station 100, returned back along the lane, relidded and passed into the rear storage cassette 108. A similar well plate feeder/stacker 113 is used for the other lane to supply well plates from the storage cassette 112 to the replating station 104 and back along the lane to the (re-)stack storage cassette 114.

The well plate feeder/stacker mechanisms including delidding are described fully in EP-A-1 293 783, the contents of which are incorporated herein by reference.

It should be noted that although the description above refers the term "well plate" in the description of the "well plate feed lane at the end of the imaging station 100", the "well plate feeder/stacker 107" and the "well plate feed storage cassette 106", the term "well plate" should be taken as limiting to a container with wells. Instead, it should be treated as a generic description of any container capable of containing cells to be picked. In the performance of the detection method described herein, for example, it will be preferable to use Petri dishes or other flat dishes for growing cells producing polypeptides to be picked. Accordingly, such dishes may be used in the apparatus described with appropriate minor modifications, if necessary.

The cell picking head 118 can thus be moved from the imaging station to the replating station to allow replating of animal cells from a target well plate to a destination well plate. The arrangement described above enables a plurality of target plates, each containing cells or colonies expressing polypeptides to be picked, in containers such as Petri dishes, to be processed at the imaging station 100 in turn. The picked cells or colonies are plated onto destination well plates at the replating station 104.

In the illustrated embodiment, there is only one destination lane. However, it may be desirable in some cases to have 2, 3 or 4 destination lanes. This may be useful when it is desired to split the animal cells from a given target well into multiple destination wells. The feeder/stacker mechanism is fully modular, so the number of well plate feed lanes can be increased without difficulty.

Figure 14:
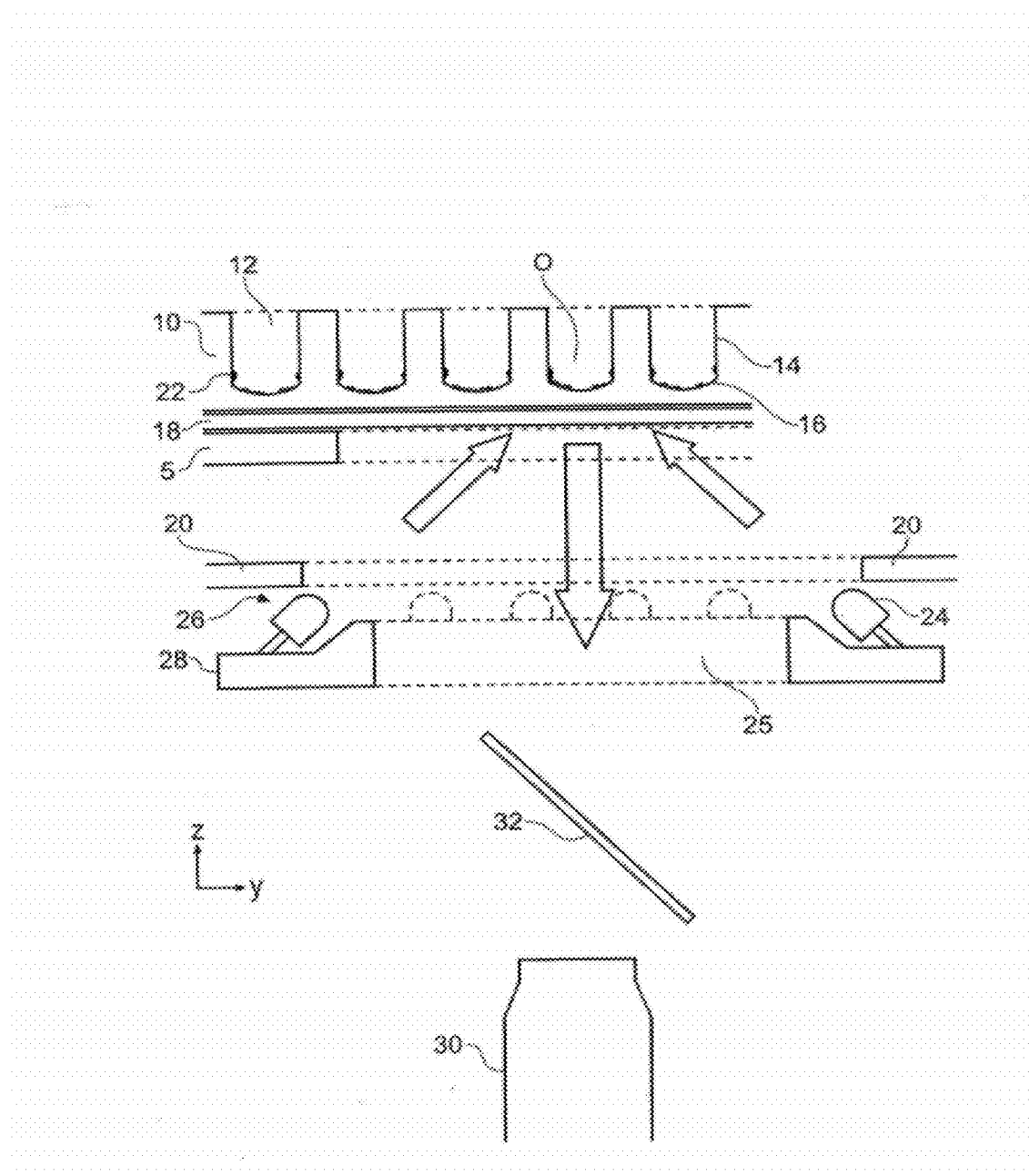
FIG. 14 is a schematic sectional side view showing the sample excitation and collection paths in the vicinity of the sample using a well plate as an example sample container.

FIG. 14 is a schematic sectional side view showing principles of the design of the optical sub-assembly 110. Part of a well plate 10 showing 5 wells is also shown. Adherent colonies 22 have been cultured in the wells also as shown, the colonies forming around the base 16 and lower sidewalls 14 of the wells 12. It will be appreciated that samples in other containers may also be studied, such as Petri dishes described above. In such containers, particularly those which contain semi-solid media such as methylcellulose, cells and colonies are growing in the media.

The imaging station is formed in an aperture in the main bed 5 covered by a sheet of optically transparent material, typically glass, that forms a light table 18. For optical analysis, a well plate 10 is arranged on the light table 18 as shown, having been deposited there by the well plate feeder/stacker. The apparatus is designed to image one well at a time. To image a specific well 12 of a well plate, the optical sub-assembly 110 is aligned relative to the well 12.

The optical sub-assembly 110 comprises two illumination sources and a collection part.

The first illumination source is formed of a plurality of white light emitting diodes (LEDs) 24 arranged to form an LED ring 26 located in a collar 28 with a central aperture 25 with the optical axes of the LEDs lying on the surface of a common cone, the point of which is coincident and labeled as the object position O in the figure. This white light source is provided principally to collect conventional images of the sample, for example as are used for performing cell confluence detection by image processing techniques. An apertured top plate 20 lying above the LED ring 26 is also illustrated. This is a structural component and has no significance for the optical design.

This second illumination source (not shown in this figure) is arranged to illuminate from the side, as shown by the sideways arrow, onto a semi-silvered mirror 32 which deflects the excitation light vertically onto the sample, as shown by the upwardly pointing arrow, in order to perform fluorescence measurements.

The collection part of the optical sub-assembly is made up of a zoom lens 30 with autofocus and is used to collect light when either (or both) of the illumination sources is used. The optical axis is vertical and coincident with the object position O.

The well to be imaged is thus aligned laterally with the optical axis of the collection optics and the fluorescence excitation optics and laterally and vertically with the center point of the white light lateral illumination, whereby the center point of the lateral illumination is around the base of the well or slightly higher as illustrated. The LEDs 24 thus illuminate a well 12 arranged in the object position O at an oblique angle from below so that an image of the well 12 is taken in a dark field configuration where light from the LEDs, if not scattered, does not contribute to the well image gathered by the collection lens 30.

Figure 15:
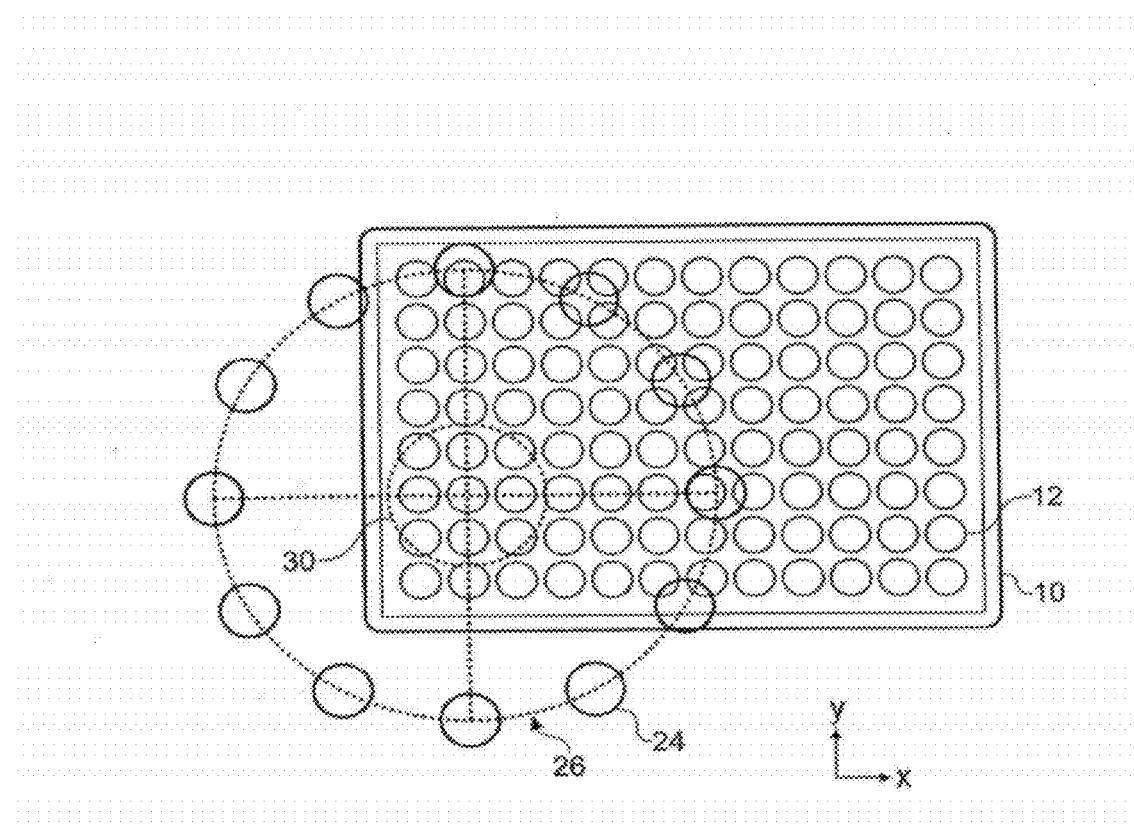
FIG. 15 is a schematic plan view of the sample vicinity with a well plate as the sample container.

FIG. 15 is a schematic plan view of selected parts of the optical system shown in FIG. 14. The well plate 10 is a 96 well version and is shown aligned with the optical sub-assembly 110 so that a well 12 three rows up (row m=3) and two columns along (column n=2) is targeted, as illustrated by the objective lens 30 and LED ring 26 of LEDs 24. The optical sub-assembly is arranged on x- and y-positioners so that the collection lens 30 and illumination ring 26 can be moved together to image any one of the wells 12. Typically, the wells will be imaged in sequence row-wise and column-wise with a rastering process. This is achieved by moving the optical sub-assembly while the well plate remains static which is preferable so that liquid in the wells is not shaken by moving the well plate between imaging each well which might have an adverse influence on the imaging.

It will be appreciated that the ability of the apparatus to image a growing container comprising a single well may be extended to enable imaging of a growing container of any suitable size. Thus, samples in other (larger) containers may also be studied, such as Petri dishes described above suitable for use in the detection method described in this document. In such dishes, the cells or colonies will be scattered more or less randomly across the surface of the plate, instead of being arranged in a row/column configuration. Nevertheless, the x- and y-positioners do not restrain the collection lens 30 and illumination ring 26 to movement in a discrete fashion, but these are instead movable continuously across the surface of the plate. Accordingly, the x- and y-positioners enable any portion of the plate to be imaged by the collection lens 30 and illumination ring 26.

Figure 16:
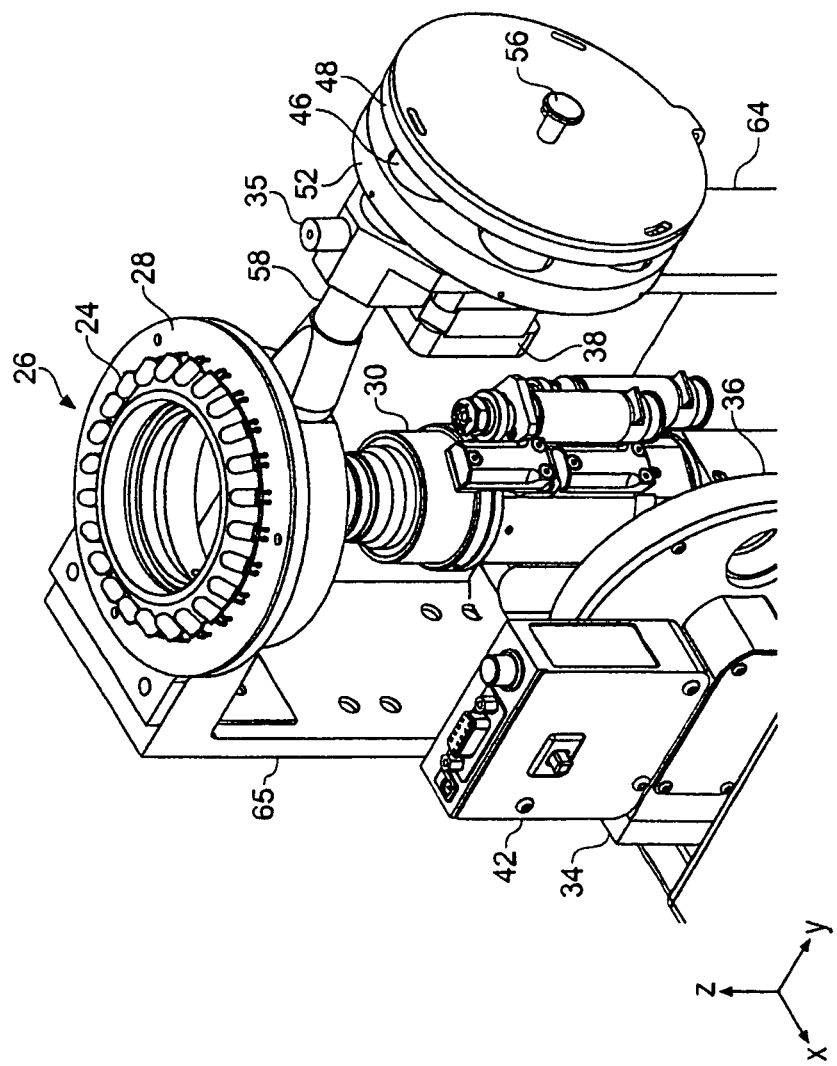
FIGS. 16, 17 and 18 are perspective and orthogonal side views of the optics sub-assembly arranged below the main bed of the apparatus of FIG. 13.
Figure 17:
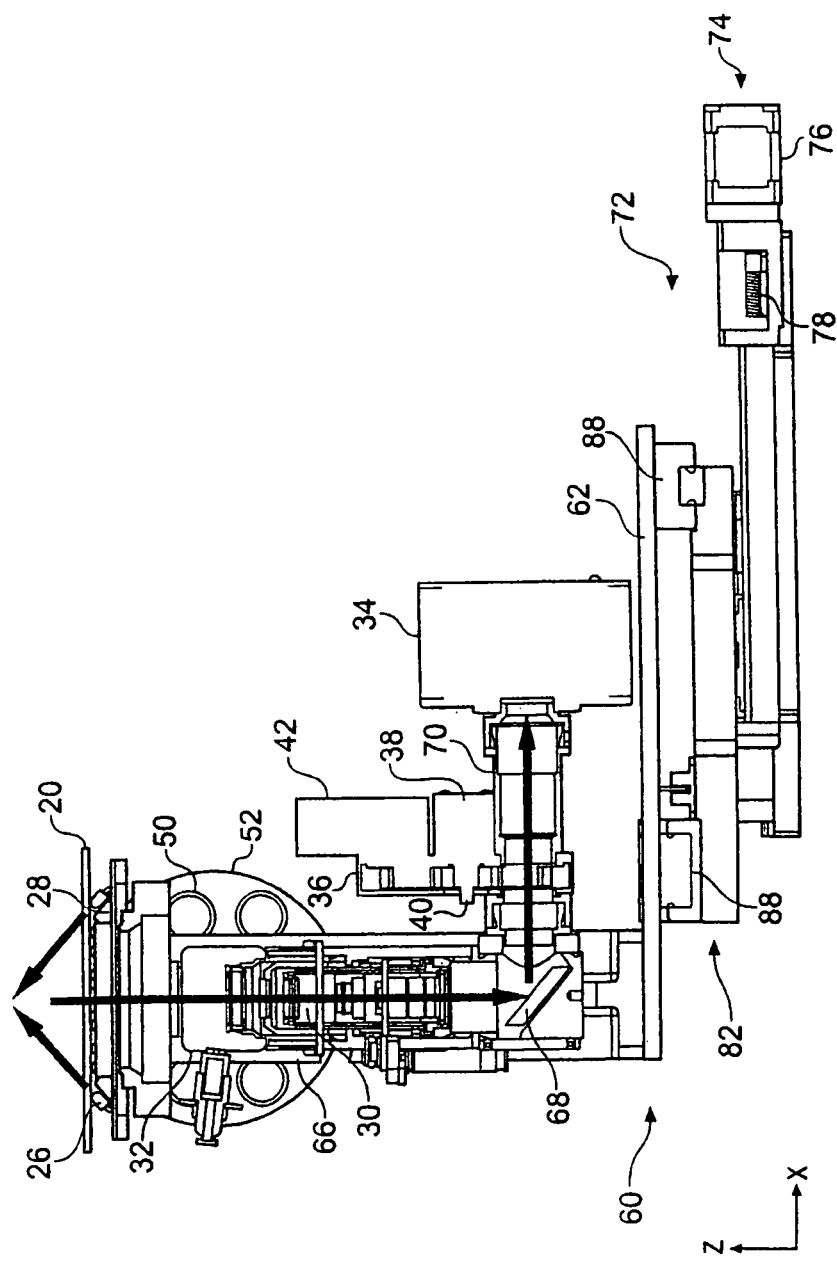
Figure 18:
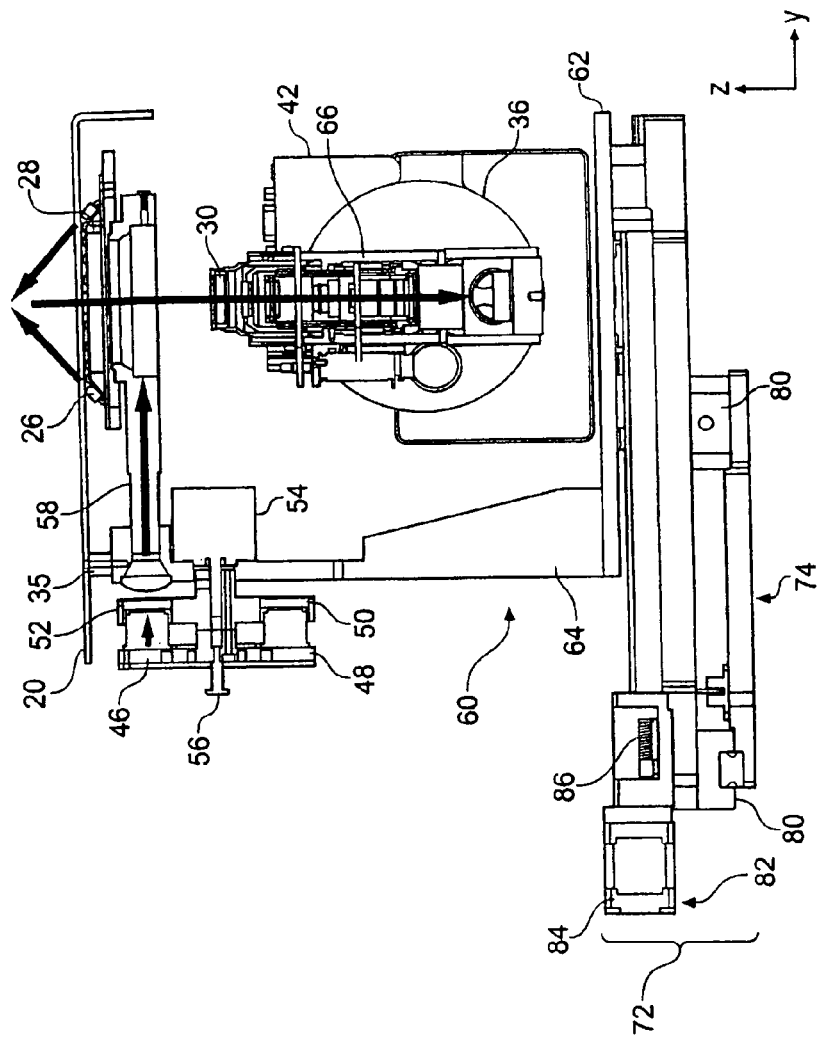

FIGS. 16, 17 and 18 are perspective and orthogonal side views of the optics sub-assembly arranged below the main bed of the apparatus of FIG. 13. These three figures are described together, rather than in turn, since they are different views of the same equipment, noting that not all features are visible or marked with reference numerals in each figure.

The previously described collar-mounted LED ring 24, 26, 28 is evident in all three figures. The LED collar 28 is cantilevered out on a side bracket from a vertical mounting plate 65 (FIG. 16) which is part of a frame 60. The vertical mounting plate 65 is upstanding from a base plate 62.

The fluorescence excitation optics is mounted on the base plate 62 via a further vertical mounting plate 64. The excitation source is colored LEDs 44 (not shown) that are arranged in groups of different colors 46 on a wheel 48 which is a converted filter wheel with LED groups 46 arranged at each filter position. In front of each LED group 46 there is a bandpass or other suitable narrowband filter 50 (see FIGS. 17 & 18) each arranged in the filter position of a further filter wheel 52 arranged coaxially and on the same motor spindle 56 as the filter wheel 48, the two wheels being driven in unison by a motor 54. Each bandpass filter 50 is selected to transmit a range of wavelengths matched to the emission wavelength band of the LED group 46 with which it is paired. Light from the uppermost LED group 46 is directed horizontally through a light pipe 58, which is not a waveguide, merely a shroud for preventing light spillage, onto the semi-silvered mirror 32 (see FIG. 17 and also FIG. 14) which serves as a beam splitter for directing a portion of the colored LED light through the LED collar's aperture 25 to the object position. Other forms of beam splitter could also be used, for example a cubic beam splitter. The beamsplitter is preferably removable, or movable away from the aperture 25 so that when lateral illumination from the colored LED groups is not needed, it can be taken out of the collection path so that it does not result in loss of collected signal. A mounting stub 35 is also evident in FIGS. 16 and 18. This mounting stub 35 is for connecting the colored LED group features to the top plate 20 (removed in FIG. 16, but shown in FIGS. 17 and 18 and also FIG. 14).

The collection lens 30 is held vertically in a mounting tube 66 (see FIGS. 17 & 18) at the base of which is arranged a plane deflecting mirror 68 which redirects the collected light horizontally and supplies it along a light pipe 70 to a CCD camera 34. Part way along the light pipe 70 there is arranged a filter wheel 36 mounted on a spindle 40 and driven by a motor 38. Drive electronics for the filter wheel 36 are housed in a unit 42. Typically filters will be used in the collection optics to filter out excitation light from the colored LED groups 46 when spectroscopic measurements are being performed. Collection side filters 45 may also be useful for filtering out fluorescence, e.g. to stop fluorescence from swamping out contrast of the cell periphery. This might be auto-fluorescence or fluorescence from a tag. For straightforward confluence detection using the white LEDs 24, no filter may be needed on the collection side.

The optical components are thus all mounted directly or indirectly on the base plate 62. The base plate 62 is carried by a linear positioner 82 which is in turn carried by a linear positioner 74 to provide xy-motion for the whole optical set-up. In the illustration, the x-positioner 74 is at the bottom with the y-positioner mounted on top of it. However, it will be appreciated this choice is arbitrary. It will also be appreciated that a parallel mechanism xy-positioner could be provided instead of two piggy-backed linear positioners. The x-positioner 74 comprises a motor 76, lead screw 78 and a pair of sets of guide bearings 80. The y-positioner 82 is the same, comprising a motor 84, lead screw 86 and a pair of sets of guide bearings 88.

As an alternative to having colored LED of different colors arranged in filter positions on a filter wheel as described above, it is possible to have concentric rings of different colors of LED in a single mounting. For example, the white light LED ring could be exchanged or supplemented with a number of LED rings of different colors. In principle an arbitrary arrangement of LEDs of different colors would provide the same functionality so long as LEDs of different colors could be driven independently, but would be a less elegant design. It would also be possible to use a single group of broadband LEDs in combination with filtering. However, this approach would tend to provide less illumination power than using different colors of LED. It will also be appreciated that other optical sources could be used including superfluorescent LEDs or diode lasers. Fixed wavelength or tunable diode lasers may be used.

By way of example, the table below gives, for a number of useful dyes, suitable LED types for the excitation LED groups 46 together with suitable pairs of excitation side filters 50 and collection-side (i.e. emission) filters 45. The peak excitation and emission wavelengths λ of the example dyes are also stated.

| Dye | Peak Excitation λ (nm) | Peak Emission λ (nm) | LED Type | Excitation Filter | Emission Filter (Chroma Co.) |
|---|---|---|---|---|---|
| BFP | 381 | 445 | UV | none | D460/50 m |
| CFP | 434 | 477 | Royal Blue | D(HQ)450/50X | D505/40 m |
| EGFP | 488 | 507 | Blue | D(HQ)470/40X | HQ535/50 m |
| FITC | 490 | 525 | Blue | D(HQ)470/40X | HQ535/50 m |
| YFP | 513 | 527 | Cyan | D(HQ)500/30X | D550/40 m |
| Rhodamine | 550 | 573 | Green | D(HQ)530/30X | HQ590/50 m |
| DSRed | 565 | 582 | Green | D(HQ)530/30X | HQ590/50 m |
| Cy5 | 649 | 670 | Red | D(HQ)623/36X | HQ700/75 m |

Figure 19:
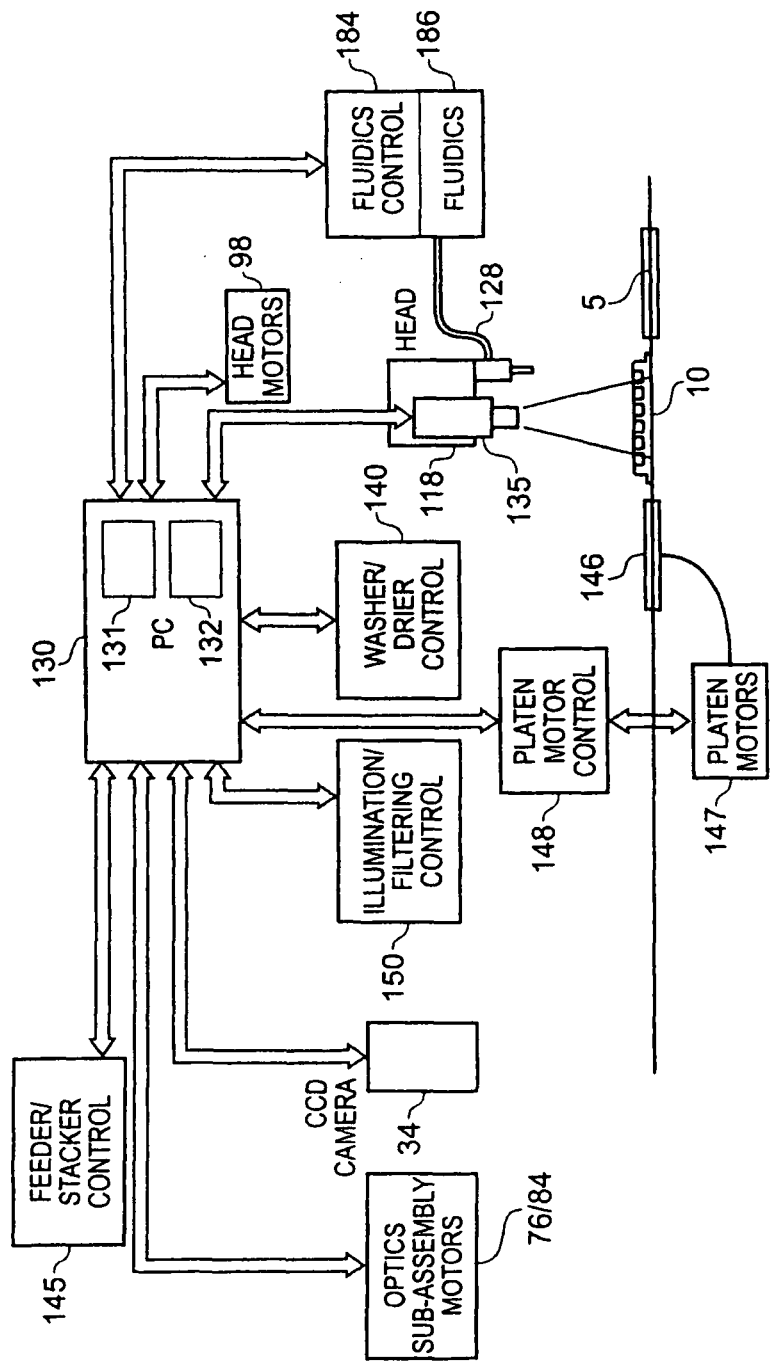
FIG. 19 is a block schematic diagram showing the control system of the apparatus.

FIG. 19 is a block schematic diagram showing the control system of the apparatus for coordinating the various components to perform the processes described above. A computer (PC 130) is used as the principal control component and is connected by electronic links using standard interfacing protocols to the various components that are part of the automated control system. The control is effected by control software 131 resident in the PC 130. Image processing and spectroscopic analysis software 132 is also resident in the PC 130 and linked to the control software 131. The image processing and spectroscopic analysis may also be carried out in hardware or firmware if desired. The CCD camera 34 is connected to the PC 130 for receiving digital images captured by the camera 34. An illumination and filter controller 150 is connected to the PC 130 for controlling the various under-bed optical sources and filter wheels of the optical sub-assembly 110. A washer/drier controller 140 is connected to the PC 130 and used to control the blower and the halogen lamps of the wash/dry station 102. The positioners 98 for moving the head 118 are connected to the PC 130. The PC 130 is also connected to the motors 76 and 84 of the x- and y-positioners of the under-bed optics sub-assembly 110. A head-mounted camera 135 is also provided for machine vision, such as bar-code detection on plates, and is connected to the PC 130 for receiving digital images captured by the head-mounted camera 135. These are used for aligning the pins of the head with the various locations of interest such as the wash/dry station 102, plates etc. The fluid lines 128 are connected to the fluidics unit 186 which is controlled by the fluidics control unit 184 connected to the PC 130. The fluidics control unit 184 is used to control the pressure in the fluid lines to allow aspiration, retention and expulsion of liquid from the sample. The fluidics control unit 184 also controls the wash cycle of the pins and fluid lines, whereby cleaning fluid from the baths is aspirated and expelled from the ends of the pins during the cleaning cycle. A feeder/stacker control unit 145 is also provided for the feeder/stacker units, including the plate supply lanes, and is connected to the PC 130. Separate units 145 may be provided for each lane in view of the modular nature of the feeder/stacker assemblies. The figure also illustrates schematically an optional feature whereby a carrier in the form of a platen 146 is provided to carry one or more plates 10 or other biological sample containers. The platen 146 is movable in the x- and y-directions by associated motors 147 and motor controller unit 148 which is connected to the PC 130, these elements collectively forming a positioning system for plates or other containers arranged on the apparatus. The platen can then be moved in a controlled fashion to allow iterative scanning by the optical system across all wells of a plate. The platen may be provided with an integral heating element, so that plates or other biological sample containers carried by the platen can be maintained at elevated temperatures, for example to promote enzymatic activity in the samples.

It will thus be appreciated that lateral positioning can be achieved in a variety of ways either by moving the optical source and detector on a common platform under the bed of the apparatus, moving the sample with its own xy-positioning system on the sample carrier, or by moving the head. In any given apparatus or process, various combinations of these motion systems may be used.

In summary, the described robotic apparatus has a sample manipulation head with associated positioning system mounted above the main bed of the apparatus, and can be used for picking of cells, in particular animal cells, or for other biological or chemical applications. An imaging station is arranged on the main bed where a sample container containing a sample can be placed in an object position. Both excitation and collection optical sub-systems are mounted under the main bed of the apparatus for performing spectroscopic analysis on a sample at the imaging station. The integration is based on a reflection mode optical solution, which allows all the optical components to be mounted under the main bed of the apparatus. Consequently, ancillary software driven or manual processes can be carried on with whether or not spectroscopic measurements are being made.

However, it will be appreciated that methods according to the invention can be performed on different apparatus than described herein. In particular, imaging tasks can be carried out in a conventional stand-alone imager, such as a Fuji LAS-1000, and picking tasks with a conventional picking robot, such as a Genetix QPix™.

In further embodiments, a cell or cell colony associated with the signal is selected by laser dissection. For instance, a focussed laser beam may be used to separate a region of the medium (or solid phase) associated with or comprising the cell or cell colony from the remainder of the medium (or solid phase). The dissected region can then be collected and subjected to further analysis, e.g. by growing or expanding cells or colonies from the dissected region. Laser dissection thus provides an alternative to traditional picking methods.

Laser dissection devices and methods are known in the art, and are described e.g. in U.S. Pat. Nos. 6,907,798 and 7,035,004. In some embodiments, the present invention may comprise the use of laser cutting or microdissection device as described in one of the above documents. The laser dissection device may be integrated with e.g. an automated imaging apparatus as described herein. For instance, a cell or cell colony associated with the signal may be identified by the imaging apparatus and automatically dissected using the laser dissection device.

In some embodiments, an image of the cells or cell colonies growing in the medium on the solid phase may be obtained, i.e. the signal is detected in the presence of the medium. In an alternative embodiment, the medium may first be removed before obtaining the image. Because the capture agent traps the polypeptide of interest on the solid phase, it is an advantage of the present method that the detection step can take place in the absence of the medium and/or cells. In such embodiments, cells or colonies may first be picked from defined locations on the plate. After removal of the medium, signal detected from defined locations on the plate can be correlated with particular colonies or cells which were picked from those locations.

Moreover, it is an advantage of the present method that cell colonies producing a polypeptide of interest in a liquid medium can be detected. Thus the method of the present invention does not necessarily require the presence of a semi-solid medium and/or the detection a halo or aura around the cell colony.

The method described herein enables colonies or cells of interest, e.g., which produce polypeptides of interest to be identified and selected. Advantageously, the colonies are visualised and imaged, and identified by software according to whether or not they emit a signal. Other characteristics, such as size, may also be used for identifying relevant colonies or cells. Selected colonies or cells may then be picked and replated, for example into 96 well plates, for growing on, using for example the ClonePix FL robotic apparatus described above.

In some embodiments, a cell or colony may also be chosen on the basis of its productivity, i.e., how much polypeptide of interest it produces. Thus, the methods described here enable the selection of high producing colonies. The method may be applied to a number of cells or colonies, preferably a plurality of cells or colonies, simultaneously, and is capable of detecting only those cells or colonies which produce the particular product of interest.

The detected signal may be processed using various methods in order to select or pick colonies of interest. In one embodiment, a production level of the polypeptide of interest may be determined, e.g. using a method as described in EP2166511. For instance, a signal level may be determined for each cell or cell colony based on signal values from a predefined area of the image comprising the cell or cell colony, the signal level being indicative of the production level of the polypeptide of interest by the cell or cell colony. Preferably, the predefined area is interior to the cell or cell or colony, e.g. cells or cell colonies are selected based on interior signal (e.g. fluorescence) intensity values. For instance, cells or cell colonies may be selected based on interior mean intensity, interior total intensity or interior mean centre intensity values, e.g. as described in EP2166511.

In an embodiment shown below, it was demonstrated that pre-coating a solid phase with a capture agent reduces the extent/size of halos, increases the average fluorescent intensity within the area of the colonies (the interior statistics) and reduces the fluorescent signal in the exterior regions. This indicates that pre-coating increases the efficiency of capture of the polypeptide of interest, and concentrates the signal near the colony. The method is therefore useful for maximizing the signal in instances where lack of fluorescence is problematic, e.g. where a colony produces a polypeptide of interest at a low level. The method may also provide a greater overall capacity to bind secreted protein, thus potentially increasing the dynamic range at the top of the scale for very high secreting colonies.

The invention will now be described by way of example only with reference to the following non-limiting embodiments.

EXAMPLES

Example 1

In this example, a CHO cell colony growing in a semi-solid medium which produces a human IgG antibody is selected, using anti-human complex initiation factor (CIF) bound to a culture plate and an FITC labelled anti-human IgG antibody.

The principle of the method is shown in FIG. 1. Essentially, at step A, the plate is pre-coated with unlabelled capture antibody. At step B, cells are plated in semi-solid medium with fluorescently-labelled detection antibody. At step C, secreted IgG is captured locally around the colony by the capture antibody and the detection antibody. An image of the plate is then obtained. By detecting the fluorescent signal, colonies secreting IgG can be identified and picked.

Optionally, colonies may be first picked and then the semi-solid medium washed off plate the plate, as shown at D. Surface-captured antibody remains on the plate and can be imaged at this stage. The image obtained of the plate after removal of the medium can be correlated with colonies picked from known locations on the plate, in order to identify high-secreting colonies.

Pre-coating of the plate with antibody leads to capture of additional secreted IgG, thereby increasing the overall fluorescence associated with a colony. IgG is also captured more efficiently (i.e. more tightly around the colony), thus resulting in a more concentrated signal and a higher signal intensity in the colony region of the plate.

Plate Coating

A 6-well suspension culture plate (available from Nunc A/S, Roskilde, Denmark, cat. no. 150239) was coated with 15 mg/ml of an unlabelled anti-human complex initiation factor (CIF) (CloneDetect K8215, available from Genetix Ltd, New Milton, UK) in filtered 1× coating buffer (available from ImmunoChemistry Technologies, Bloomington, Minn., cat. no. 6245). CIF is a capture agent which is capable of binding to, and forming a complex with, secreted human IgG. The coating solution was removed after 2 hours incubation at room temperature and followed with a 2× wash using PBS. XP Media CHO (a liquid medium for CHO—S cells, available from Genetix Ltd, cat. no. K8750) was added (2 ml per well) followed by incubating at room temperature for 1 hour to block non-specific binding.

Cell Plating

A low secretory CHO cell line B13 was plated in Clone-Media CHO (a semi-solid medium for CHO—S cells, available from Genetix Ltd, cat. no. K8710) with an FITC labelled anti-human IgG antibody (CloneDetect K8200, available from Genetix Ltd). The FITC-labelled antibody is a detection agent in this example. Cells were plated at 1800 cells per well in an uncoated 6-well plate or a plate pre-coated with CIF as described above. The B13 cell line secretes a human IgG antibody.

After 12-days plating, cells were imaged using various instruments (ClonePix FL, available from Genetix Ltd; a Leica microscope or Leica macroscope).

Effect of Pre-Coating on Fluorescent Signal

Figure 2:
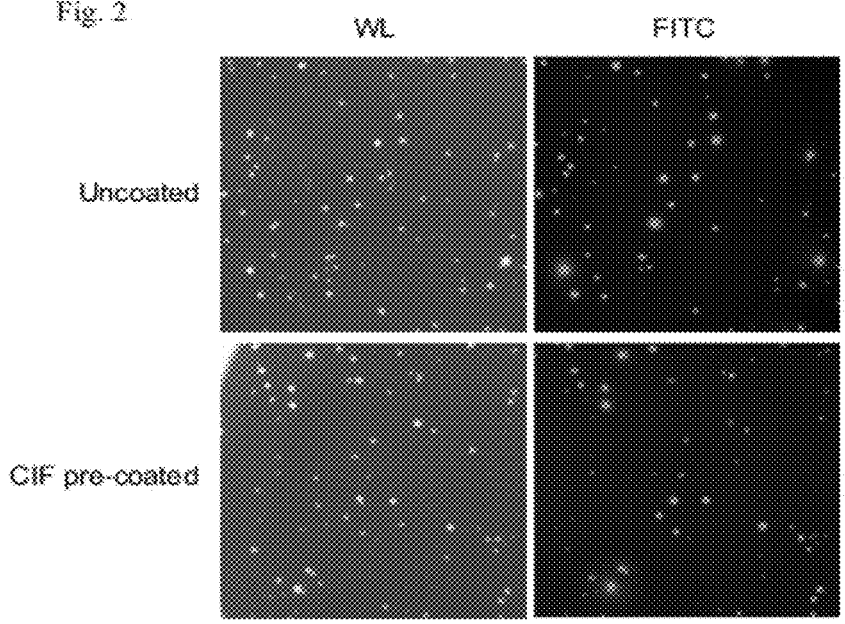
FIG. 2 shows images of colonies in semi-solid media obtained using ClonePix FL imaging, under either white (WL) or fluorescent (FITC) light.

FIG. 2 shows images of colonies in semi-solid media obtained using ClonePix FL imaging, under either white (WL) or fluorescent (FITC) light. Halos around colonies appear less pronounced in capture antibody (CIF) pre-coated plates.

Figure 3:
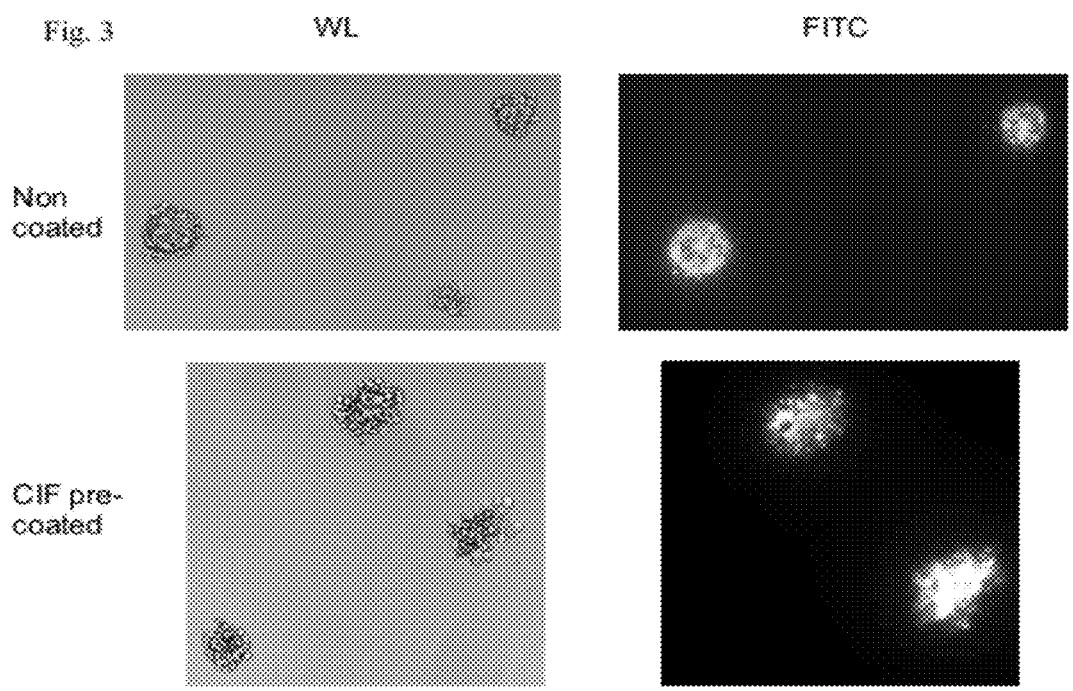
FIG. 3 shows images of colonies in semi-solid media obtained using microsope imaging, under either white (WL) or fluorescent (FITC) light.

FIG. 3 shows images of colonies in semi-solid media obtained using microscope imaging, under either white (WL) or fluorescent (FITC) light. As shown in FIG. 2, the halos which appear around colonies on non-coated plates are less pronounced in plates pre-coated with capture antibody (CIF).

The fluorescent (FITC) signal associated with colonies growing in semi-solid media was quantified from the images using ClonePix FL. Non-secreting colonies (i.e. colonies with no fluorescent signal) were gated out and statistics for remaining colonies (3 repeats for each condition) were exported for further analysis. The degree of statistical significance between comparison data sets was determined by unpaired Student's t-test (each data set contained >500 data points). The results are shown in Table 1 below.

TABLE 1

| Statistics* (FITC signal) | Non-coated | | CIF coated | | % change in signal | P value |
| --- | --- | --- | --- | --- | --- | --- |
| | Mean | SEM | Mean | SEM | | |
| Interior Mean Intensity | 3,322.35 | 66.79 | 3,895.90 | 64.60 | 17.2% | $p < 5.1137E{-}10$* |
| Interior Total Intensity | 426,560.63 | 7,690.00 | 457,621.10 | 7,881.67 | 7.3% | $p < 0.002$* |
| Interior | 4,548.62 | 70.683 | 5632.11 | 83.86 | 23.8% | $p < 1.096E{-}17$* |

TABLE 1-continued

| Statistics* (FITC signal) | Non-coated Mean | Non-coated SEM | CIF coated Mean | CIF coated SEM | % change in signal | P value |
|---|---|---|---|---|---|---|
| Mean Centre Intensity | | | | | | |
| Exterior Mean Intensity | 1,113.01 | 33.04 | 1,092.77 | 30.03 | −1.8% | p < 0.325 |
| Exterior Total Intensity | 397,556.17 | 12,026.45 | 390,707.87 | 11,392.38 | −1.7% | p < 0.339 |
| Normalized Intensity | 6,689.23 | 158.48 | 6,850.73 | 147.12 | 2.4% | p < 0.227 |
| Sum Total Intensity | 774,202.69 | 18,785.96 | 803,903.58 | 18,211.10 | 3.8% | p < 0.128 |

*The derivation of these statistical parameters is described in EP2166511.

The results show that total fluorescent intensity associated with colonies increased slightly in capture antibody pre-coated plates compared with untreated plates. However, exterior fluorescence intensity values for colonies decreased slightly in pre-coated plates, whereas interior fluorescence intensity values showed a highly significant increase. Interior intensity statistics reflect the fluorescent signal derived from within the area of the cell colony itself, whereas exterior intensity values relate to the fluorescent signal associated with but external to the cell colony, i.e. the signal associated with a halo or aura around the cell colony.

These results indicate that pre-coating with a capture antibody leads to increased retention of secreted IgG within the immediate vicinity of secreting colonies, and reduces the formation of an aura or halo around the colony. The increased internal fluorescence signal facilitates the identification and picking of secreting colonies. In particular, the increased detectable signal may increase the dynamic range enabling the highest secreting colonies to be better distinguished from the next highest secretors, whilst also enabling the detection of low-secreting colonies which might otherwise be poorly detectable.

Picking and Re-Imaging

All colonies were picked using ClonePix FL, the semi-solid medium was washed off using PBS and empty plates were re-imaged.

Figure 4:
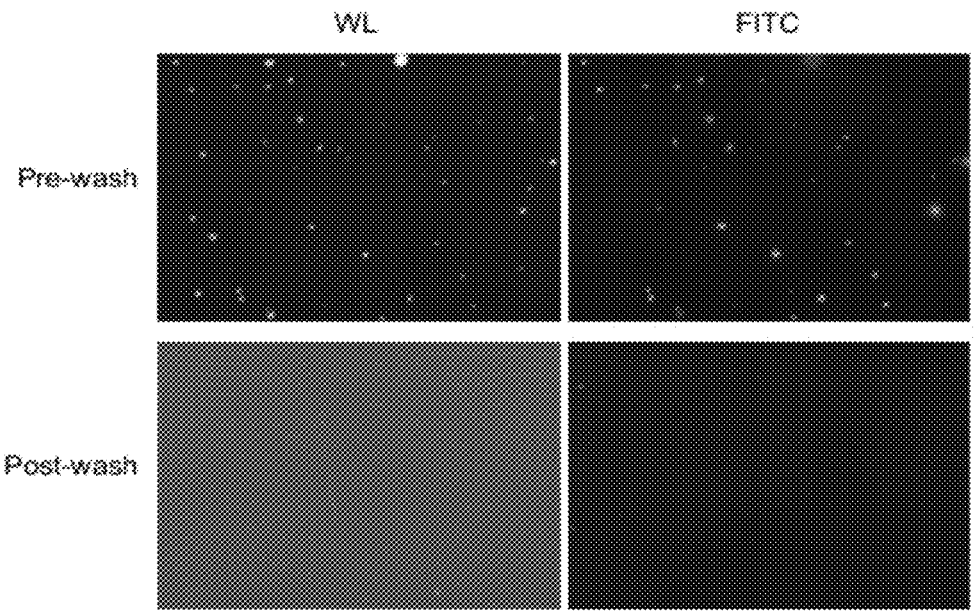
FIG. 4 shows non-coated plates imaged using ClonePix FL under white (WL) and fluorescent (FITC) light, before and after the semi-solid medium was removed.

FIG. 4 shows non-coated plates imaged using ClonePix FL under white (WL) and fluorescent (FITC) light, before and after the semi-solid medium was removed.

Figure 5:
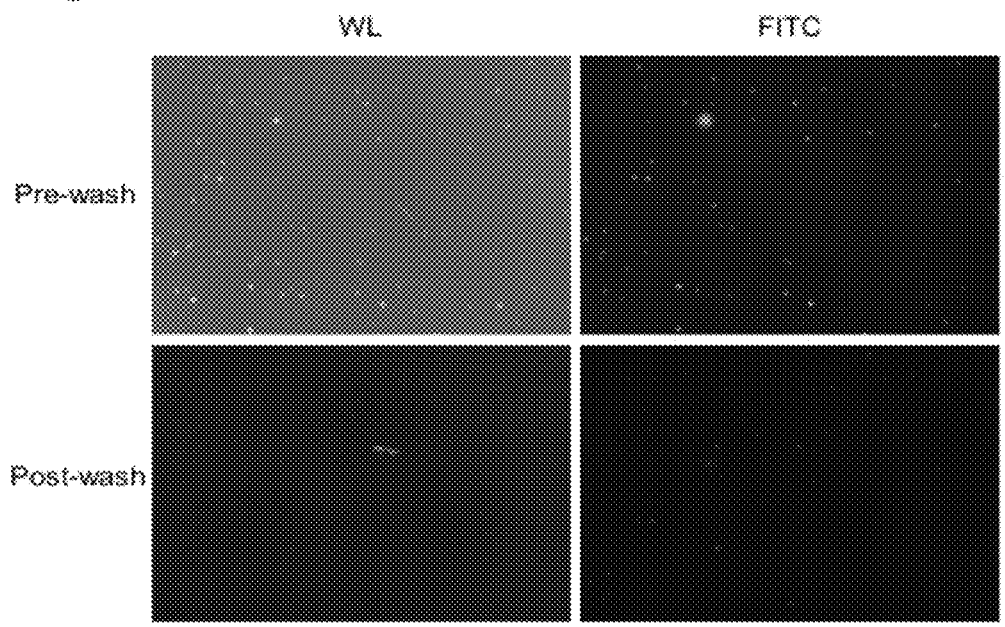
FIG. 5 shows capture antibody (CIF) coated plates imaged using ClonePix FL under white (WL) and fluorescent (FITC) light, before and after the semi-solid medium was removed.

FIG. 5 shows capture antibody (CIF) coated plates imaged using ClonePix FL under white (WL) and fluorescent (FITC) light, before and after the semi-solid medium was removed.

It is apparent from FIG. 4 that after removal of the semi-solid medium, no labelled antibody remains on the plate. However, FIG. 5 shows that in plates pre-coated with capture antibody, labelled antibody remains on the plate and is detectable at positions corresponding to secreting colonies even after removal of the semi-solid medium.

Figure 6:
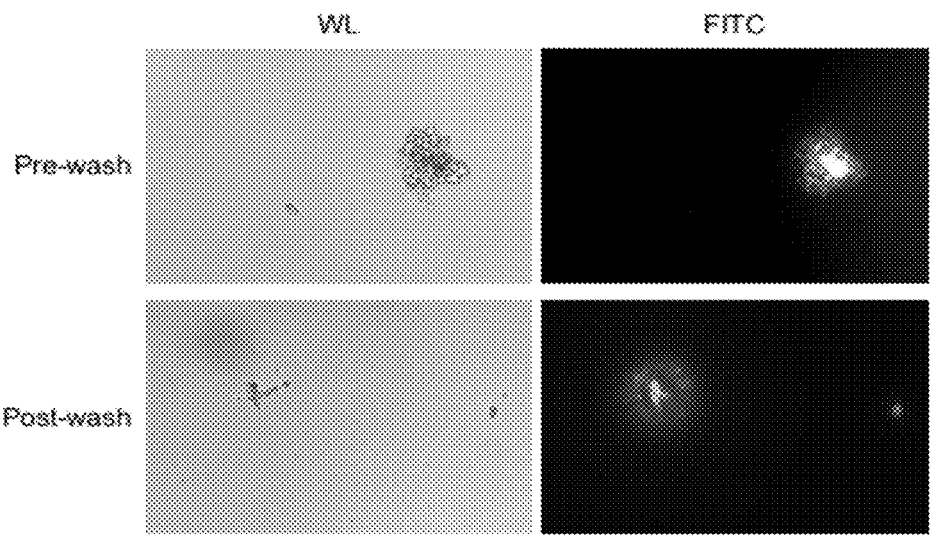
FIG. 6 shows capture antibody coated plates imaged using a microscope under white (WL) and fluorescent (FITC) light, before and after the semi-solid medium was removed.

FIG. 6 shows capture antibody coated plates imaged using a microscope under white (WL) and fluorescent (FITC) light, before and after the semi-solid medium was removed.

Figure 7:
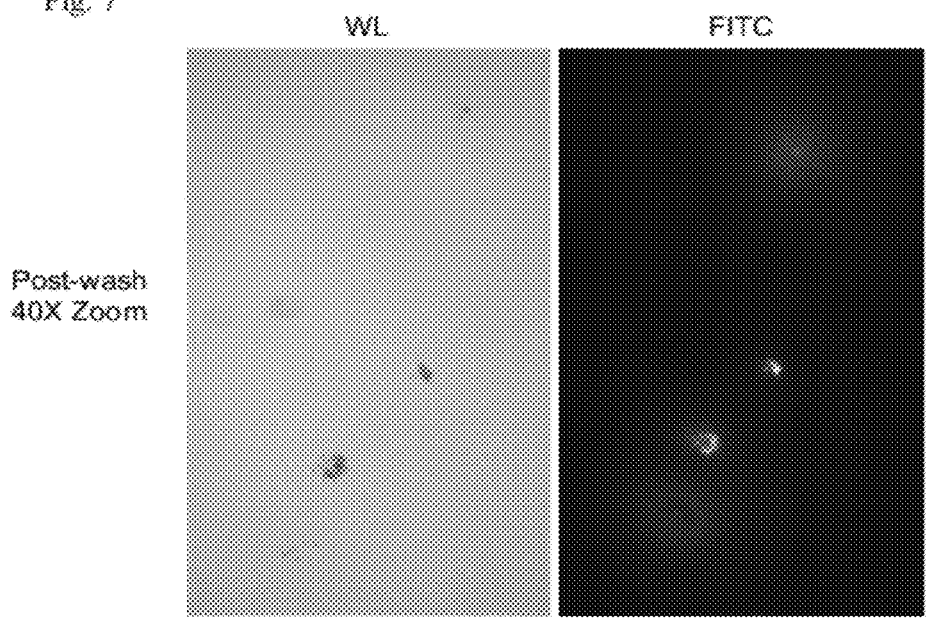
FIG. 7 shows capture antibody coated plates imaged using a macroscope under white (WL) and fluorescent (FITC) light, after the semi-solid medium has been removed.

FIG. 7 shows capture antibody coated plates imaged using a macroscope under white (WL) and fluorescent (FITC) light, after the semi-solid medium has been removed.

In both FIGS. 6 and 7, fluorescence derived from labelled antibody bound to the plate is clearly detectable following removal of semi-solid medium. This demonstrates that plates can be imaged following picking of colonies and removal of semi-solid medium. High-producing colonies can be identified by associating positions showing fluorescence in the image of the medium-free plate with colonies picked from the corresponding positions.

Example 2

In this Example, the method of Example 1 was repeated but using a liquid medium in place of the semi-solid medium. 6-well suspension culture plates (Nunc A/S) were coated with anti-human CIF (CloneDetect K8215) as described in Example 1. B13 adherent cells in XP Media CHO (a liquid medium for CHO—S cells available from Genetix Ltd) were plated at 250 cells/ml with an FITC labelled anti-human IgG antibody (CloneDetect K8200).

10 days after plating, images were taken using various instruments.

Figure 8:
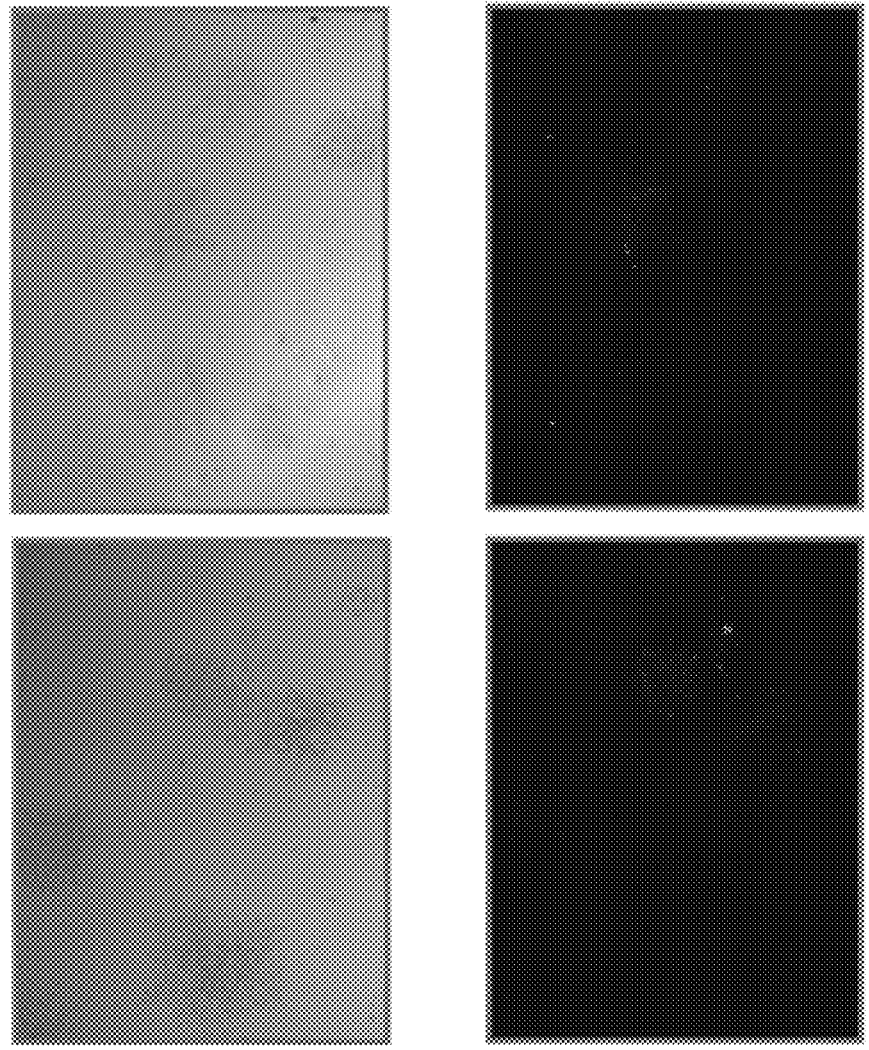
FIG. 8 shows images of colonies in a liquid medium on non-coated plates taken using a microscope with 10× magnification, under bright field and fluorescent (FITC) imaging.

FIG. 8 shows images of colonies in a liquid medium on non-coated plates taken using a microscope with 10× magnification, under bright field and fluorescent (FITC) imaging. The FITC signal is very low, and few colonies are visible.

Figure 9:
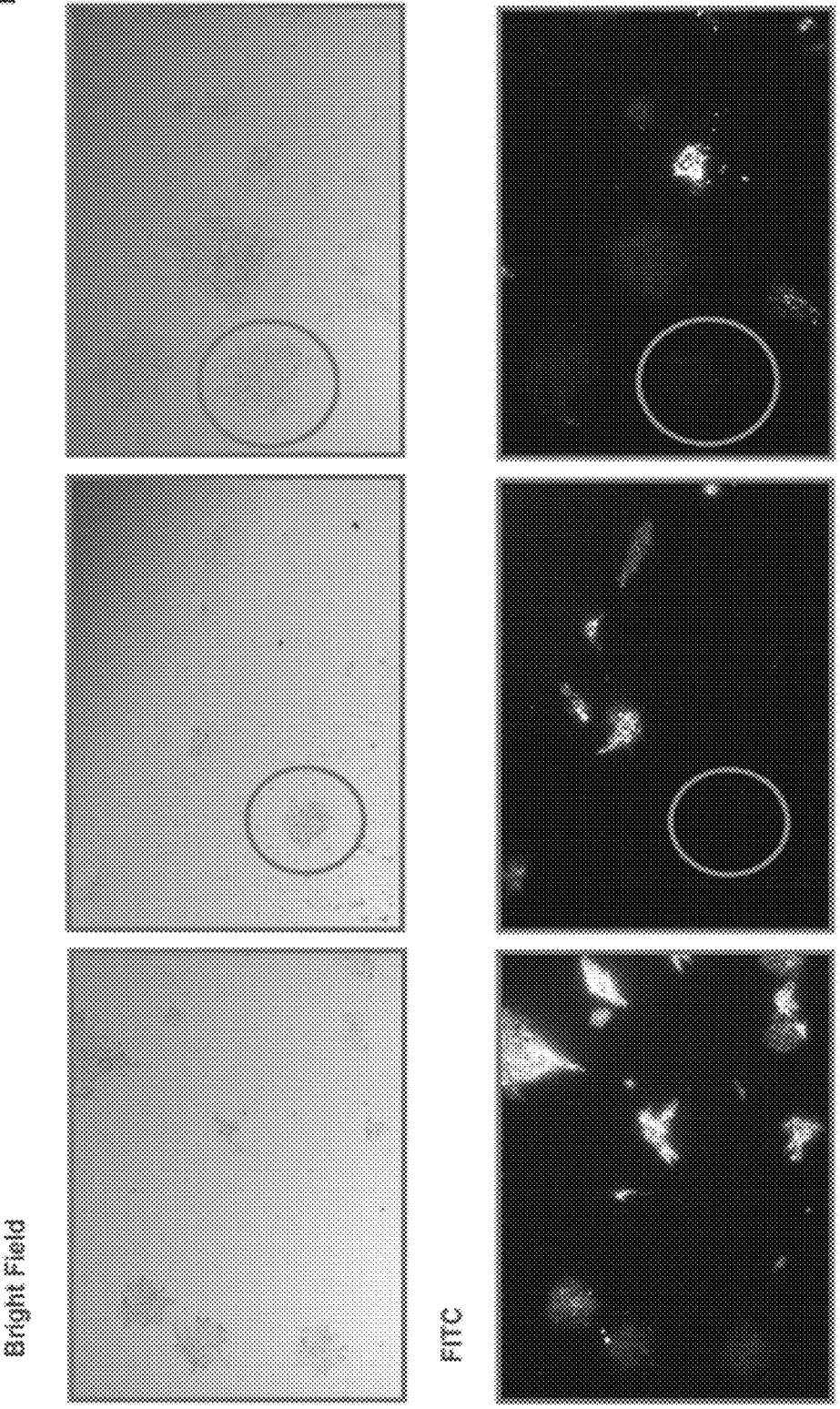
FIG. 9 shows images of colonies in a liquid medium on capture antibody (CIF) coated plates taken using a microscope with 10× magnification, under bright field and fluorescent (FITC) imaging

FIG. 9 shows images of colonies in a liquid medium on capture antibody (CIF) coated plates taken using a microscope with 10× magnification, under bright field and fluorescent (FITC) imaging. Adherent cell colonies which are highly fluorescent are clearly visible, corresponding to colonies which produce high levels of IgG. Other colonies are visible under white light but show low fluorescence, indicating low levels of IgG secretion.

Figure 10:
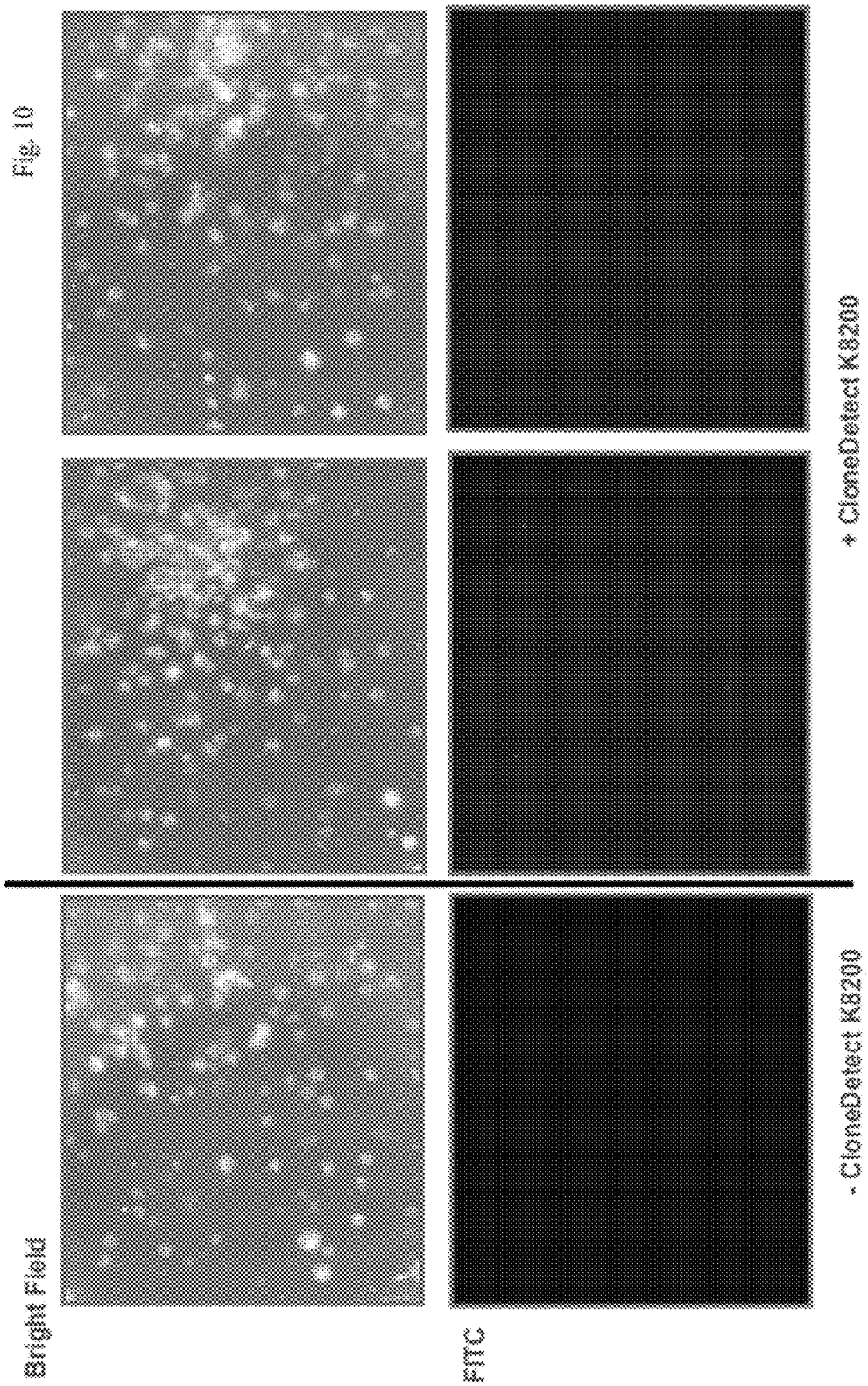
FIG. 10 shows colonies in a liquid medium on non-coated plates imaged using ClonePix FL, using bright field and fluorescent (FITC) imaging.

FIG. 10 shows colonies in a liquid medium on non-coated plates imaged using ClonePix FL, using bright field and fluorescent (FITC) imaging. The FITC signal is barely detectable both in the presence and absence of the detection antibody (CloneDetect K8200), with few detectable colonies.

Figure 11:
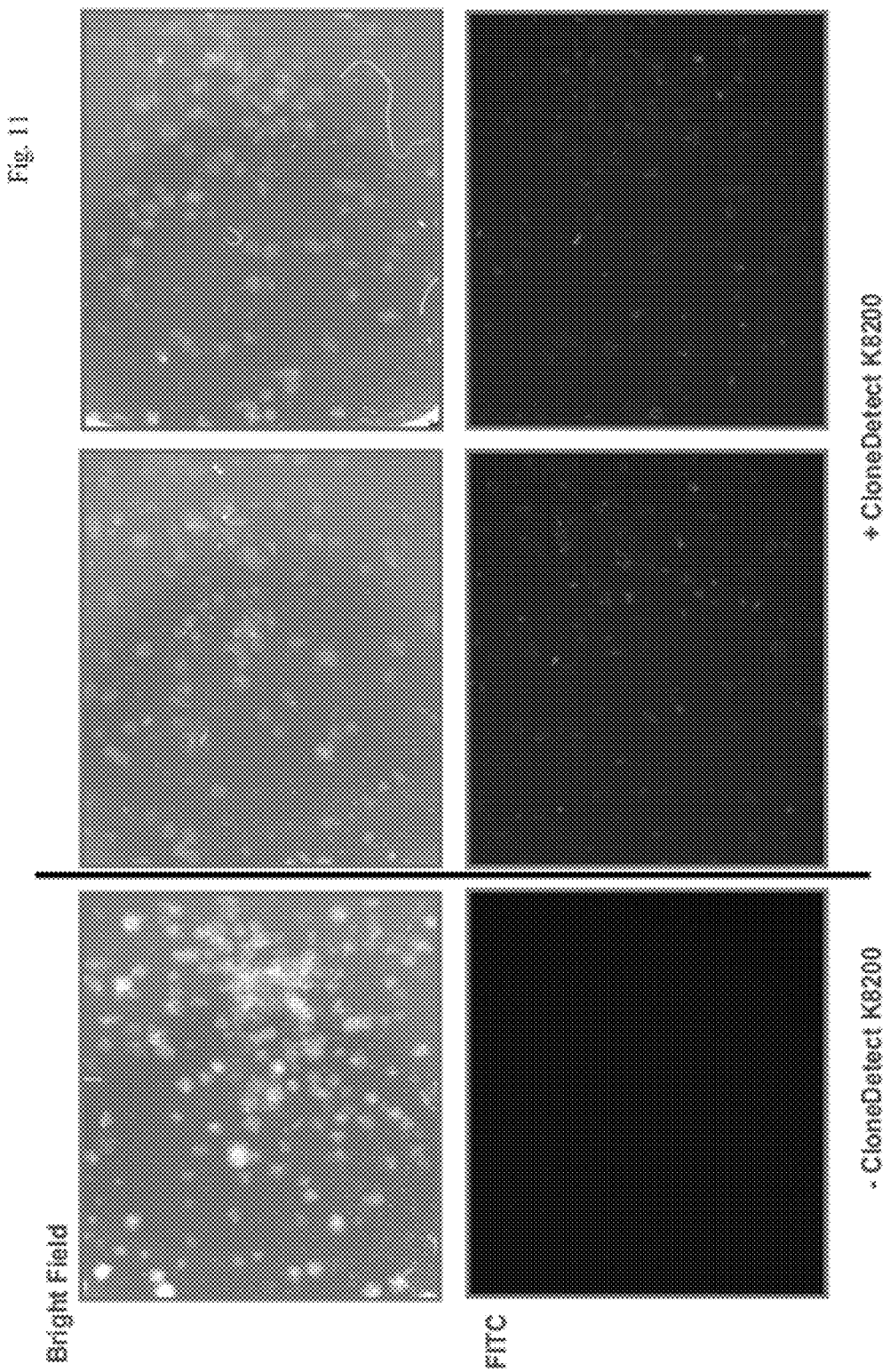
FIG. 11 shows colonies in a liquid medium on capture antibody (CIF) coated plates imaged using ClonePix FL, using bright field and fluorescent (FITC) imaging.

FIG. 11 shows colonies in a liquid medium on capture antibody (CIF) coated plates imaged using ClonePix FL, using bright field and fluorescent (FITC) imaging. In the presence of detection antibody (CloneDetect K8200), highly fluorescent IgG secreting colonies are visible.

Figure 12:
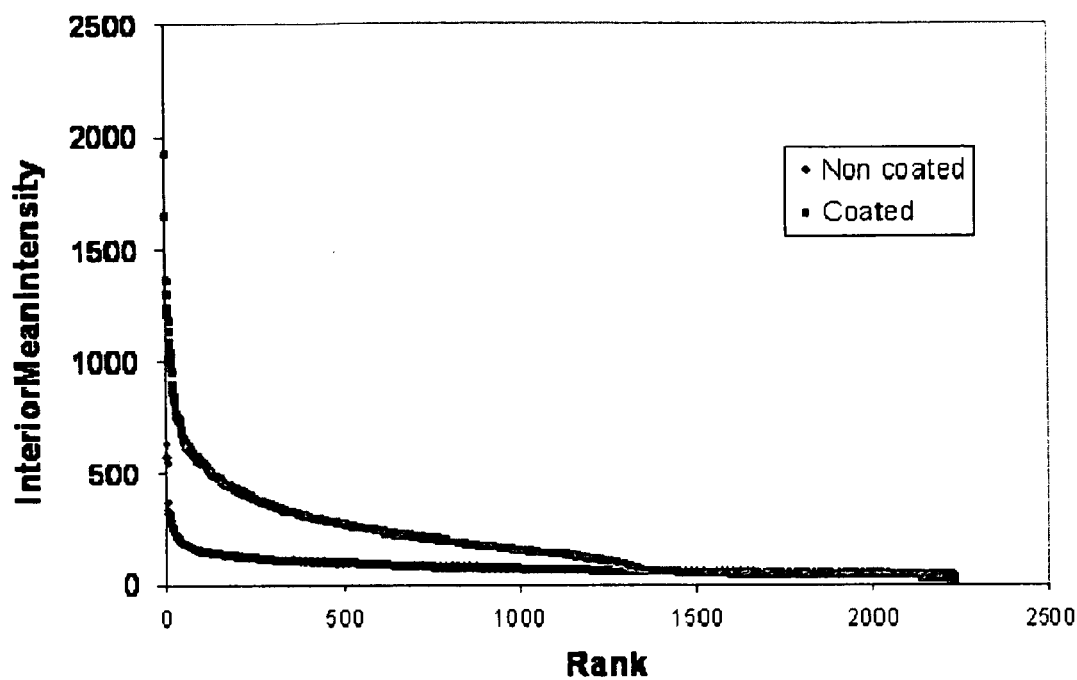
FIG. 12 shows interior mean fluorescent (FITC) intensity values for colonies growing in liquid media on non-coated and capture antibody coated plates, quantified using ClonePix FL.

The fluorescent (FITC) signal associated with colonies growing in liquid media on non-coated and capture antibody coated plates was quantified from the images using ClonePix FL. The interior mean fluorescent intensity was determined for each colony, and colonies placed in rank order for each of the capture antibody coated and non-coated data sets. The results are shown in FIG. 12. This figure indicates that coating the plate with capture antibody makes many more IgG-secreting colonies selectable using fluorescent imaging, particularly when interior fluorescent intensity is calculated.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods* in Enzymology, Academic Press; Using Antibodies : A Laboratory Manual : Portable Protocol NO. I by Edward Harlow, David Lane, Ed Harlow (1999, Cold Spring Harbor Laboratory Press, ISBN 0-87969-544-7); Antibodies : A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

The invention claimed is:

1. A method for selecting a cell or cell colony which produces a polypeptide of interest, comprising:
   a) providing a medium comprising cells and a detection agent capable of binding to the polypeptide of interest;
   b) providing a solid phase having a capture agent disposed thereon, wherein the capture agent is capable of binding to the polypeptide of interest;
   c) contacting the medium with the solid phase having the capture agent disposed thereon;
   d) detecting a signal produced by the detection agent bound to the polypeptide which is captured by the capture agent on the solid phase, wherein the solid phase comprises a culture dish, a well or a plate; and
   e) selecting a cell or cell colony generating a level of the signal that indicates the cell or cell colony has produced the polypeptide of interest which has been captured adjacent the cell or cell colony by the capture agent disposed on the solid phase, and bound by the detection agent.

2. The method according to claim 1, wherein the medium comprises a liquid medium.

3. The method according to claim 1, wherein the medium comprises a semi-solid medium.

4. The method according to claim 1, wherein step (e) comprises picking a cell or cell colony which produces the polypeptide of interest.

5. The method according to claim 4, wherein the cell or cell colony, or a surface of the cell or cell colony, is picked by an automated cell picking device.

6. The method according to claim 1, wherein step (d) comprises obtaining an image formed by the signal, and analysing the image to detect signal values above a predetermined level.

7. The method according to claim 6, comprising determining a signal level for each cell or cell colony based on signal values from a predefined area of the image comprising the cell or cell colony, the signal level being indicative of the production level of the polypeptide of interest by the cell or cell colony.

8. The method according to claim 6, wherein the cell or cell colony is selected in step (e) based on signal intensity values representing an interior of the cell or cell colony.

9. The method according to claim 6, wherein the image is obtained and analysed by an automated imaging system.

10. The method according to claim 1, wherein the signal is a fluorescent signal.

11. The method according to claim 1, wherein fluid of the medium is removed before detecting the signal.

12. The method according to claim 1, wherein the polypeptide of interest is secreted by the cell or cell colony.

13. The method according to claim 1, wherein the polypeptide of interest is an immunoglobulin.

14. The method according to claim 13, wherein the polypeptide of interest is an IgG.

15. The method according to claim 1, wherein the detection agent comprises an antibody or fragment thereof, or protein A or protein G, which binds selectively to the polypeptide of interest.

16. The method according to claim 1, wherein the detection agent comprises a fluorescent label.

17. The method according to claim 1, wherein the capture agent comprises an antibody or fragment thereof, or protein A or protein G, which binds selectively to the polypeptide of interest.

18. The method according to claim 1, wherein step (e) comprises selecting the cell or cell colony by laser dissection.

19. A method for selecting a cell or cell colony which produces a polypeptide of interest, the method comprising:
   a) providing a medium;
   b) disposing cells and a detection agent in the medium, the detection agent being capable of binding to the polypeptide of interest;
   c) providing a solid phase having a capture agent immobilized thereon, wherein the capture agent is capable of binding to the polypeptide of interest;
   d) contacting the medium in step b) with the solid phase in step c);
   e) detecting a signal generated by the detection agent after the cells and the detection agent have been disposed in the medium and after contact has been performed between the medium and the solid phase, wherein the signal is generated by the detection agent bound to the polypeptide which is captured by the capture agent on the solid phase, wherein the solid phase comprises a culture dish, a well or a plate; and
   f) selecting a cell or cell colony generating a level of the signal that indicates the cell or cell colony has produced the polypeptide of interest, which has been captured adjacent the cell or cell colony by the capture agent immobilized on the solid phase, and bound by the detection agent.

20. The method of claim 19, wherein the cells and the detection agent are disposed in the medium before contact is performed between the medium and the solid phase.

* * * * *